United States Patent [19]

Kawaguchi et al.

[11] Patent Number: 5,616,441
[45] Date of Patent: Apr. 1, 1997

[54] TRYPTOANTHORINE DERIVATIVE CONTAINED IN ELECTROPHOTOSENSITIVE MATERIAL

[75] Inventors: Hirofumi Kawaguchi; Yasufumi Mizuta; Syunichi Matsumoto; Nobuko Akiba; Toshiyuki Fukami; Ichiro Yamazato; Hisakazu Uegaito; Yuji Tanaka, all of Osaka, Japan

[73] Assignee: Mita Industrial Co., Ltd., Osaka, Japan

[21] Appl. No.: 527,776

[22] Filed: Sep. 13, 1995

[30]     Foreign Application Priority Data

Sep. 20, 1994   [JP]   Japan ..................................... 6-225184
Feb. 28, 1995   [JP]   Japan ..................................... 7-039639
Feb. 28, 1995   [JP]   Japan ..................................... 7-039642

[51] Int. Cl.$^6$ ........................................................ G03G 5/06
[52] U.S. Cl. ................................................. 430/78; 544/246
[58] Field of Search ..................... 430/78, 76; 544/246

[56]              References Cited

U.S. PATENT DOCUMENTS 5,116,706   5/1992   Kojima et al. ............................. 430/78
5,420,259   5/1995   Guentner et al. .

FOREIGN PATENT DOCUMENTS 0513558   11/1992   European Pat. Off. .
281050    10/1913   Germany .
4114990   11/1992   Germany .
61-134354  6/1986   Japan .
1-206349   8/1989   Japan .
4-295853  10/1992   Japan .

OTHER PUBLICATIONS

Chemical Abstracts 121:241714.
Borsenberger, Paul M. & Paul S. Weiss. Organic Photoreceptors for Imaging Systems. New York: Marcel–Dekker, Inc. pp. 190–211.
Bergman, et al., *Tetrahedron Letters*, No. 30, pp. 2625–2626, 1977.
WO–A–95/13807, May 26, 1995.
Database Beilstein Online (no date), Beilstein Registry #257325
European Search Report, Feb. 9, 1996.

*Primary Examiner*—Christopher D. Rodee
*Attorney, Agent, or Firm*—Beveridge, DeGrandi, Weilacher & Young, L.L.P.

[57]               ABSTRACT

According to the present invention, there is provided a novel tryptoanthorine derivative represented by the formula:

wherein $R^{1a}$, $R^{1b}$, $R^{1c}$, $R^{1d}$, $R^{2a}$, $R^{2b}$, $R^{2c}$, and $R^{2d}$ are the same or different and indicate a hydrogen atom, an alkyl group or a halogenated alkyl group; provided that $R^{1a}$, $R^{1b}$, $R_{1c}$ and $R^{1d}$ do not indicate a hydrogen atom, simultaneously. Tryptoanthorine and a derivative thereof are suitably used for an electrophotosensitive material because of their excellent electron transferring capability.

8 Claims, 2 Drawing Sheets

TRYPTOANTHORINE DERIVATIVE CONTAINED IN ELECTROPHOTOSENSITIVE MATERIAL

BACKGROUND OF THE INVENTION

The present invention relates to a novel tryptoanthorine derivative and an electrophotosensitive material which is used for image forming apparatuses such as copying apparatus and laser beam printer.

In the image forming apparatuses such as copying apparatus, an organic photosensitive material such as an organic photoconductor (OPC) having a sensitivity within the wavelength range of a light source of the apparatus has exclusively been used.

As the organic photoconductor, a multi-layer type photoconductor comprising an electric charge generating layer and an electric charge transferring layer, which are mutually laminated, is well known, but a single-layer type photoconductor wherein an electric charge generating material and an electric charge transferring material are dispersed in the same layer is also known.

Although a high carrier mobility are required to the electric charge transferring material to be used for these photoconductors, almost all of electric charge transferring materials having a high carrier mobility are hole transferring materials having hole transferring properties and, therefore, only negative charging type multi-layer type organic photoconductors, which are provided with an electric charge transferring layer at their outer layer from the viewpoint of mechanical strength, are used for practical application. However, since the negative charging type organic photoconductor utilizes negative-polarity corona discharge, problems such as large amount of ozone generated, environmental pollution, deterioration of photosensitive material, etc. have arisen.

Accordingly, in order to eliminate the above drawbacks, it has been studied to use an electron transferring material as the electric charge transferring material. In Japanese Unexamined Patent Publication No. 1-206349, there is suggested that a compound having a diphenoquinone structure is used as the electron transferring material for electrophotosensitive material.

However, it is difficult for electron transferring materials such as diphenoquinones to match with the electric charge generating material, which results in insufficient injection of electrons from the electric charge generating material into electron transferring material. Therefore, sufficient photosensitivity could not be obtained.

Furthermore, if the single-layer and dispersion type organic photoconductor can be used, a lot of advantages can be obtained, e.g. easy production of the photoconductor, prevention of coat failure, improvement of optical characteristics, etc. However, the single-layer type organic photosensitive layer had a problem that the electron transfer is inhibited by an interaction between diphenoquinone and an hole transferring material.

On the other hand, in Japanese Unexamined Patent Publication No. 4-295853, there is suggested that an electrophotosensitive material having a high sensitivity is made by the combination of an electron transferring material of 3,5-dimethyl-3',5'-di-t-butyl-4,4'-diphenoquinone, a hole transferring material of alkyl substituted triphenyldiamine, etc., and an electric charge generating material of a phthalocyanine pigment. However, the resulting photosensitive material is insufficient in wear resistance.

Furthermore, in Japanese Unexamiend Patent Publication No. 61-134354, there is disclosed a 3,3'-dimethylbenzidine derivative as a compound having a high hole transferring capability. However, this derivative normally has a low melting point (about 180° C. or less) and, therefore, the photosensitive layer obtained using the derivative has a low glass transition temperature, and durability and heat resistance of the photosensitive material are insufficient.

Furthermore, regarding the polarity of the photosensitive material to be charged, the scope of application of the photosensitive material can be widen if one photosensitive material can be used for both positive charging and negative charging types. However, such a photosensitive material has never been put into practice.

SUMMARY OF THE INVENTION

It is a main object of the present invention is to solve the above technical problem, thereby providing a novel compound which is suitable as electron transferring materials in electrophotosensitive material, etc.

It is another object of the present invention to provide an electrophotosensitive material wherein the injection and transfer of electrons from an electric charge generating material are smoothly conducted, and therefore sensitivity is improved in comparison with a conventional one.

It is still another object of the present invention is to provide an electrophotosensitive material having an organic photosensitive layer which is superior in wear resistance.

It is a further object of the present invention to provide an electrophotosensitive material which is superior in durability and heat resistance, wherein a glass transition temperature of a photosensitive layer is sufficiently high.

The present inventors have studied intensively in order to accomplish the above objects. As a result, it has been found that tryptoanthorine represented by the formula (2):

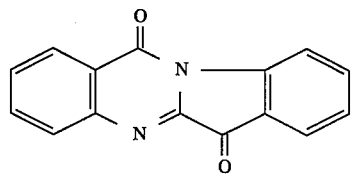

(2)

which is a known substance as a pigment intermediate has a high electron transferring capability in comparison with a conventional diphenoquinone compound and is superior in function as the electron transferring material. That is, the above-described tryptoanthorine is good in solubility to solvent and superior in compatibility with binding resin and, further, it is superior in matching with an electron generating material (pigment), thereby injecting electrons smoothly. Furthermore, it is particularly superior in electron transferring properties in the low electric filed.

Therefore, the present inventors have further studied intensively on the basis of the above-described tryptoanthorine in order to develop a compound which is suitable as the electron transferring material. As a result, it has been found that a tryptoanthorine derivative represented by the formula (1):

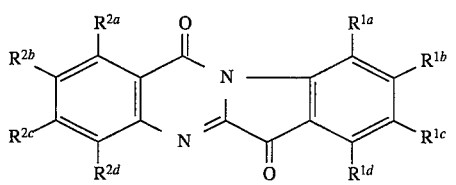

wherein $R^{1a}$, $R^{1b}$, $R^{1c}$, $R^{1d}$, $R^{2a}$, $R^{2b}$, $R^{2c}$ and $R^{2d}$ are the same or different and indicate a hydrogen atom, an alkyl group or a halogenated alkyl group; provided that $R^{1a}$, $R^{1b}$, $R^{1c}$ and $R^{1d}$ do not indicate a hydrogen atom, simultaneously, is superior to the above-described tryptoanthorine (2) in solubility to solvent and compatibility with binding resin and, therefore, the resulting photosensitive material shows a higher electron transferring capability, thus the present invention has been accomplished.

That is, the tryptoanthorine derivative of the present invention is represented by the formula (1).

Such a derivative of the present invention can also be used for applications such as solar battery, EL element, etc. utilizing its high electron transferring capability. Furthermore, the derivative of the present invention is secure in view of carcinogenicity.

Furthermore, when using the tryptoanthorine derivative represented by the formula (1) as the electron transferring material in the electrophotosensitive material, there can be provided an organic photosensitive material having a high sensitivity.

In the electrophotosensitive material of the present invention, tryptoanthorine represented by the formula (2) can also be used, in addition to the tryptoanthorine derivative represented by the formula (1). In that case, there can be provided an organic photosensitive material having a high sensitivity.

Accordingly, the electrophotosensitive material of the present invention comprises a conductive substrate, and an organic photosensitive layer provided on the conductive substrate and containing a tryptoanthorine represented by the following formula (3) or a derivative thereof.

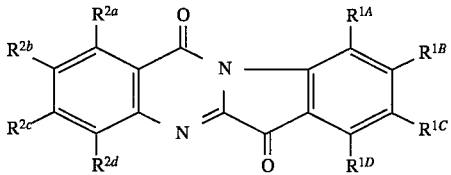

wherein $R^{1A}$, $R^{1B}$, $R^{1B}$ and $R^{1D}$ are the same or different and indicate a hydrogen atom, an alkyl group or a halogenated alkyl group; and $R^{2a}$, $R^{2b}$, $R^{2c}$ and $R^{2d}$ are as defined above.

This tryptoanthorine or its derivative of the formula (3) includes the tryptoanthorine derivative represented by the formula (1) and tryptoanthorine represented by the formula (2).

The tryptoanthorine or its derivative (3) has a π electron conjugate system which is spreaded more than that of a diphenoquinone derivative which has hitherto been used as the electron transferring material, and shows a high electron transferring capability. Furthermore, it is good in solubility to solvent and compatibility with binding resin, and is also superior in matching with electric charge generating material. This matching with the electric charge generating material becomes more excellent by introducing an alkyl group or a halogenated alkyl group as a substituent of the compound of the formula (3).

Accordingly, when using the tryptoanthorine or its derivative (3) as the electron transferring material in the electrophotosensitive material, electrons are smoothly injected from the electron charge generating material and the electron transferring properties in the low electric field are improved and, at the same time, the proportion of electrons to holes to be recombined is decreased and the apparent electric charge-generating efficiency approaches the practical value, which results in improvement of the sensitivity of the photosensitive material. Furthermore, the residual potential of the photosensitive material becomes low, which results in improvement of the stability and durability at the time of repeating of exposure.

The preferred organic photosensitive layer in the present invention comprises a binding resin, an electric charge generating material, an electron transferring material of a tryptoanthorine or a derivative thereof represented by the formula (3) and a hole transferring material of a phenylenediamine derivative represented by the formula:

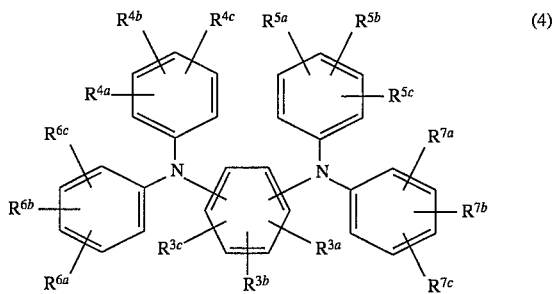

wherein $R^{3a}$, $R^{3b}$, $R^{3c}$, $R^{4a}$, $R^{4b}$, $R^{4c}$, $R^{5a}$, $R^{5b}$, $R^{5c}$, $R^{6a}$, $R^{6b}$, $R^{6c}$, $R^{7a}$, $R^{7b}$ and $R^{7c}$ are the same or different and indicate a hydrogen atom, an alkyl group, an aryl group which may have a substituent, an alkoxy group or a halogenated alkoxy group.

That is, by using the phenylenediamine derivative having a specific structure represented by the formula (4) as the hole transferring material in combination with the electron transferring material, there can be obtained an electrophotosensitive material which is superior in not only sensitivity but also wear resistance.

Furthermore, another preferred organic photosensitive layer in the present invention comprises a binding resin, an electric charge generating material, an electron transferring material of a tryptoanthorine or its derivative represented by the formula (3), and at least one hole transferring material selected from the group consisting of a benzidine derivative represented by the formula:

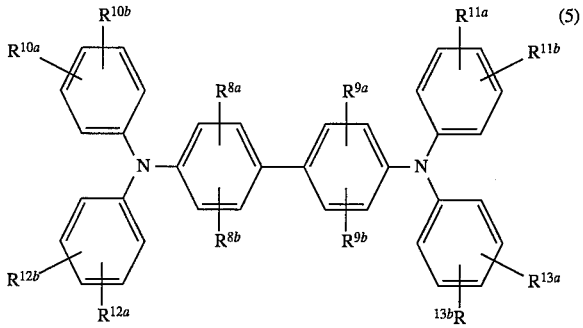

wherein $R^{8a}$, $R^{8b}$, $R^{9a}$ and $R^{9b}$ are the same or different and indicate a hydrogen atom or an alkyl group; and $R^{10a}$, $R^{10b}$, $R^{11a}$, $R^{11b}$, $R^{12a}$, $R^{12b}$, $R^{13a}$ and $R^{13b}$ are the same or different and indicate an alkyl group,

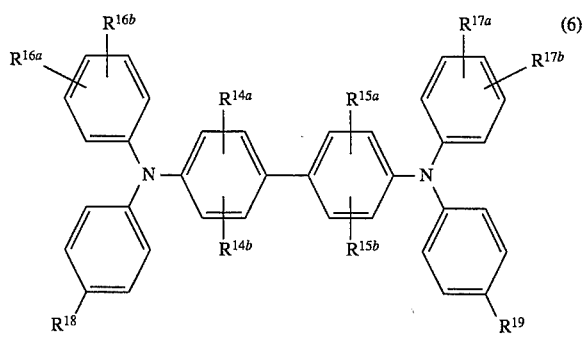

wherein $R^{14a}$, $R^{14b}$, $R^{15a}$ and $R^{15b}$ are the same or different and indicate a hydrogen atom or an alkyl group; $R^{16a}$, $R^{16b}$, $R^{17a}$ and $R^{17b}$ are the same or different and indicate an alkyl group; and $R^{18}$ and $R^{19}$ are the same or different and indicate an alkyl group having 3 to 5 carbon atoms or an aryl group which may have a substituent, and

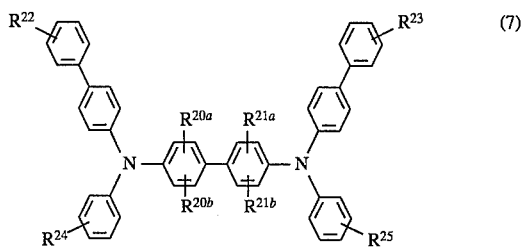

wherein $R^{20a}$, $R^{20b}$, $R^{21a}$, $R^{21b}$, $R^{22}$ and $R^{23}$ are the same or different and indicate a hydrogen atom or an alkyl group; and $R^{24}$ and $R^{25}$ are the same or different and indicate a hydrogen atom, an alkyl group or an aryl group which may have a substituent.

That is, the benzidine derivatives (5), (6) and (7) having a specific chemical structure have a high hole transferring capability, a good compatibility with binding resin and a high melting point, and it has no action for inhibiting an electron transfer carried out by the electron transferring material. Accordingly, by using at least one of the benzidine derivatives (5), (6) and (7) with the above-described electron transferring material, there can be obtained an electrophotosensitive material which has a low residual potential and an excellent sensitivity, and which is sufficiently high in glass transition temperature of the photosensitive layer and is also superior in durability and heat resistance.

Furthermore, the organic photosensitive layer may further contains an electron accepting compound having an oxidation-reduction potential of –0.8 to –1.4 V.

As the electron generating material, a phthalocyanine pigment is suitably used.

DETAILED DESCRIPTION OF THE INVENTION

Figure 1:
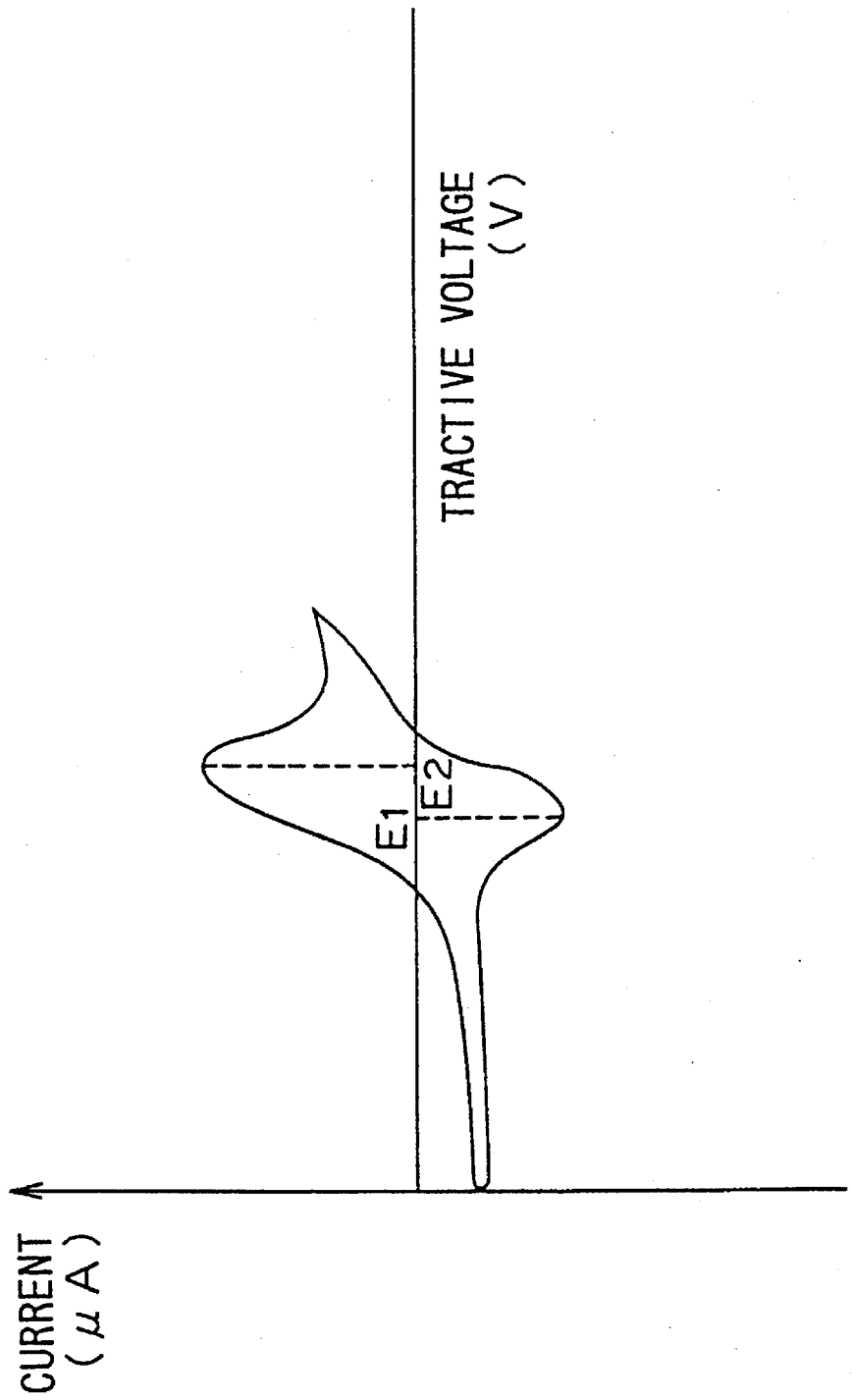
FIG. 1 is a graph illustrating a relation between the tractive voltage (V) and current (A) for determining the oxidation-reduction potential in the present invention.

Examples of the alkyl group include alkyl groups having 1 to 6 carbon atoms, such as methyl group, ethyl group, n-propyl group, isopropyl group, n-butyl group, secondary butyl group, tertiary butyl group, pentyl group, hexyl group and the like.

The halogenated alkyl group is obtained by substituting the above-described alkyl group with fluorine, chlorine, bromine or iodine, but the substitution position and number of the halogen atom are not specifically limited. Examples thereof include trifluoromethyl, 1,2-dichloroethyl, 1-bromo-t-propyl, periodo-t-butyl, etc.

In the formula (1), the proviso "$R^{1a}$, $R^{1b}$, $R^{1c}$ and $R^{1d}$ do not indicate a hydrogen atom, simultaneously" means that at least one of $R^{1a}$, $R^{1b}$, $R^{1c}$ and $R^{1d}$ is an alkyl group or a halogenated alkyl group.

The derivative represented by the formula (3) is, as is shown by the following reaction scheme, synthesized by reacting a derivative of isatoic acid anhydride represented by the formula (8) with an isatin derivative represented by the formula (9) in a suitable solvent. The derivative represented by the formula (1) included in the formula (3) is also synthesized according to the same manner as that described above.

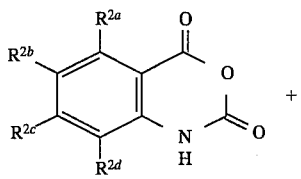

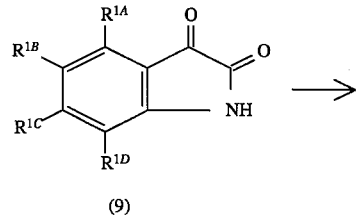

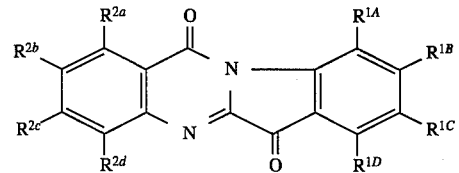

wherein $R^{1A}$ to $R^{1D}$ and $R^{2a}$ to $R^{2d}$ are as defined above.

Examples of the solvent to be used for the above reaction include dimethylformamide, dimethyl sulfoxide, pyridine, chloroform, tetrahydrofuran, etc. The reaction may be normally conducted at a temperature of 40° to 130° C. for about 1 to 8 hours.

The isatin derivative (9) can be synthesized, for example, as shown in the following reaction scheme. That is, an aqueous solution obtained by adding chloral and hydroxylammonium chloride to hydrochloride of an aniline derivative (10) as a starting material is reacted for 0.5 to 2 hours with heating at 70° to 110° C. to give an isonitrosoacetanilide derivative, and this product is cyclized with concentrated sulfuric acid and hydrolyzed to give an isatin derivative (9).

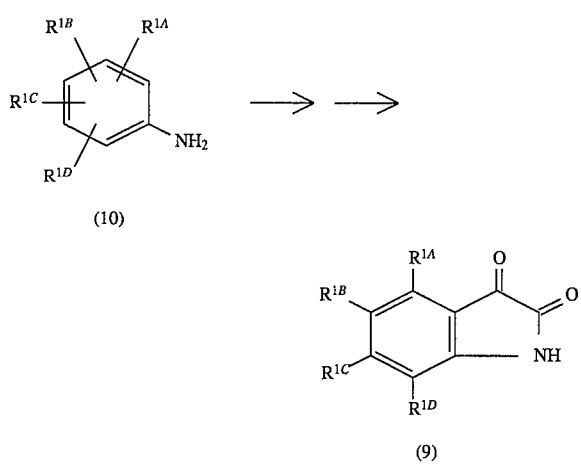

(10)

(9)

wherein $R^{1A}$ to $R^{1D}$ are as defined above.

On the other hand, the derivative (8) of isatoic acid anhydride can be synthesized as shown in the following reaction scheme. That is, it is obtained by using the isatin derivative (9') as the starting material to react with concentrated sulfuric acid and hydrogen peroxide in a solvent (acetic acid, etc.) The isatin derivative (9') is obtained according to the same manner as mentioned above. The reaction is conducted at a temperature of room temperature to 70° C. for 1 to 4 hours. In addition, it can also be obtained by reacting an anthranil derivative acid or an anthranilic derivative with ethyl chloroformate or reacting sodium anthranilate with phosgene.

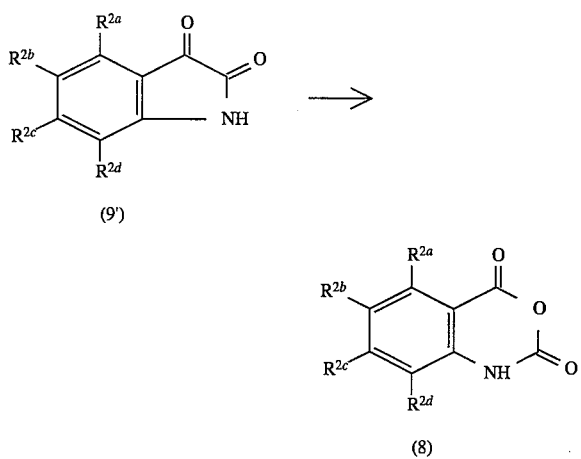

(9')

(8)

wherein $R^{2a}$ to $R^{2d}$ are as defined above.

Among the compounds represented by the formula (1) of the present invention, a derivative having the most simple structure is a compound wherein at least one of $R^{1a}$ to $R^{1d}$ is an alkyl group and $R^{2a}$ to $R^{2d}$ indicate a hydrogen atom, simultaneously. This compound shows a high electron transferring capability as is apparent from the Examples as described later, and is superior in solubility to solvent and compatibility with binding resin. The other compounds of the present invention have also the same advantage.

Hereinafter, the electrophotosensitive material of the present invention will be explained.

The electrophotosensitive material of the present invention comprises an organic photosensitive layer provided on a conductive substrate. This organic photosensitive layer contains a tryptoanthorine derivative represented by the formula (3) as the electron transferring material in a binding resin.

The organic photosensitive layer is classified into two types, that is, a single-layer type photosensitive layer containing the electron transferring material together with an electric charge generating material and a hole transferring material, and a multi-layer type photosensitive material containing the electric charge transferring layer and electric charge generating layer. Furthermore, it is possible for the photosensitive material of the present invention to use as positive charging or negative charging type. It is particularly preferred to use as the positive charging type.

In the positive charging type photosensitive material, electrons emitted from the electron generating material in the exposure process are smoothly injected into the electron transferring material and then transferred to the surface of the photosensitive layer by actions of the giving and receiving of electrons between electron transferring materials to cancel the positive electric charge (+) which has previously been charged on the surface of the photosensitive layer. On the other hand, holes (+) are injected into the hole transferring material and transferred to the surface of the conductive substrate without being trapped on the way, and then holes are canceled by the negative charge (−) which has previously been charged on the surface of the conductive substrate. It is considered that the sensitivity of the positive charging type photosensitive material is improved in this manner. In the negative charging type photosensitive material, the sensitivity is also improved, similarly, although the direction of the electric charge to be transferred becomes reverse.

As the hole transferring material, there can be used hole transferring materials which have hitherto been known, and examples thereof include nitrogen-containing cyclic compounds and condensed polycyclic compounds, e.g. diamine compounds, oxadiazole compounds such as 2,5-di(4-methylaminophenyl)-1,3,4-oxadiazole, etc.; styryl compounds such as 9-(4-diethylaminostyryl)anthracene, etc.; carbazole compounds such as polyvinyl carbazole, etc.; organic polysilane compounds; pyrazoline compounds such as 1-phenyl-3-(p-dimethylaminophenyl)pyrazoline, etc.; hydrazone compounds, triphenylamine compounds, indole compounds, oxazole compounds, isoxazole compounds, thiazole compounds, thiadiazole compounds, imidazole compounds, pyrazole compounds, triazole compounds, etc.

Preferred examples of the hole transferring material to be used in the present invention include N,N,N',N'-tetrakis(p-methylphenyl)-3,3'-dimethylbenzidine, 1,1-bis(4-diethylaminophenyl)-4,4-diphenyl-1,3-butadiene, N-ethyl-3-carbazolylaldehyde diphenylhydazone, p-N,N-diethylbenzaldehyde diphenylhydazone, 4-[N,N-bis(p-tolyl)amino]-β-phenylstilbene, etc.

These hole transferring materials are used alone or in combination thereof. Furthermore, when using the hole transferring material having film forming properties, such as polyvinyl carbazole, a binding resin is not necessarily required.

Among the above hole transferring materials, those having an ionization potential of 4.8 to 5.8 eV, preferably 5.0 to 5.6 eV are used. Furthermore, those having an electric charge mobility of not less than $1 \times 10^{-6}$ cm$^2$/V second at an electric field of $3 \times 10^5$ V/cm are particularly preferred. When using the hole transferring material of which ionization potential and electric charge mobility are within the above ranges, it is possible to further decrease the residual potential of the photosensitive material to improve the sensitivity.

The value of the ionization potential is measured in air using an atomosperic photoelectron analytical apparatus (AC-1, manufactured by Riken Kiki Co., Ltd.).

In the present invention, the reason why the residual potential of the photosensitive material can be decreased to improve the sensitivity by using the hole transferring material having the ionization potential within the above range is not necessarily apparent, but is considered as follows.

That is, an ease of injecting of electric charges into the hole transferring material from the electric charge generating material is closely related to the ionization potential of the hole transferring material. When the ion potential of the hole transferring material is larger than the above range, the degree of the injection of electric charges into the hole transferring material from the electric charge generating material becomes low, or the degree of the giving and receiving of holes between hole transferring materials becomes low. Therefore, it is admitted that the sensitivity is deteriorated.

On the other hand, in the system wherein the hole transferring material and electron transferring material coexist, it is necessary to pay attention to an interaction between both materials, e.g. formation of an electric charge moving complex. When such a complex is formed between both materials, a recombination is formed between holes and electrons and the mobility of electric charges is generally deteriorated. When the ionization potential of the hole transferring material is smaller than the above range, a tendency to form a complex between the hole transferring material and electron transferring material becomes large and the recombination between electrons and holes is formed. Therefore, it is considered that the apparent quantum yield is deteriorated, which results in deterioration of sensitivity. Accordingly, the ionization potential of the hole transferring material is preferably within the above range.

In the present invention, it is preferred to use the phenylenediamine derivative represented by the formula (4) as the hole transferring material in order to improve the wear resistance of the photosensitive layer.

In the compound of the formula (4), examples of the alkyl group include the same groups as those described above. Examples of the aryl group include phenyl group, naphthyl group, anthryl group, phenanthryl group, etc. Examples of the alkoxy group include methoxy group, ethoxy group, n-propoxy group, isopropoxy group, n-butoxy group, s-butoxy group, t-butoxy group, n-pentyloxy group, n-hexyloxy group, etc. The halogenated alkoxy group may be those which are obtained by substituting the above alkoxy groups with halogen atoms such as fluorine, chlorine, bromine, iodine, etc. The substitution position and number of the substituent excluding the hydrogen atom is not specifically limited, and it is preferred that at least one of three groups of $R^{4a}$, $R^{4b}$ and $R^{4c}$; $R^{5a}$, $R^{5b}$ and $R^{5c}$; $R^{6a}$, $R^{6b}$ and $R^{6c}$; and $R^{7a}$, $R^{7b}$ and $R^{7c}$, which are substituted on four benzene rings except a center benzene ring, is a substituent other than hydrogen atom.

Examples of the substituent which may be substituted to the aryl group in formulae (4), (6) and (7) include an alkyl group, an alkoxy group, a halogen atom, etc.

Examples of the phenylenediamine derivative (4) include the compounds represented by the following formulas (4-1) to (4-6).

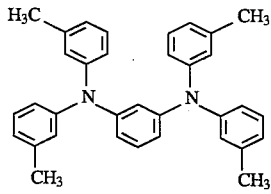
(4-1)

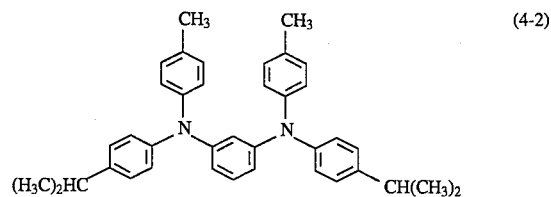
(4-2)

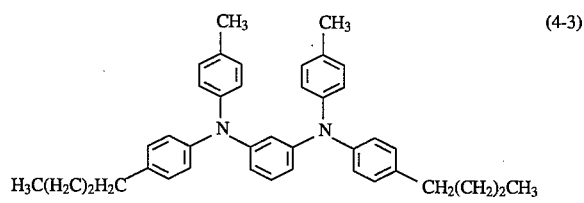
(4-3)

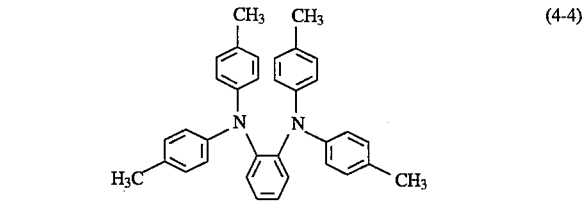
(4-4)

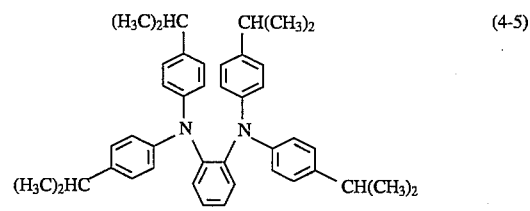
(4-5)

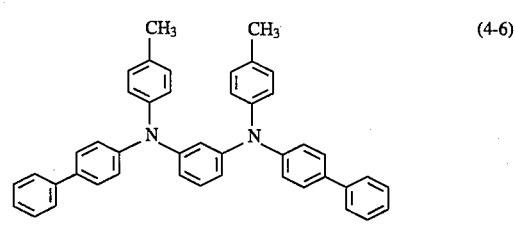
(4-6)

The phenylenediamine derivative (4) can be synthesized by various methods. For example, in the synthesis of the phenylenediamine derivative represented by the formula (4-2), as shown in the following reaction scheme, N,N'-diacetyl-1,3-phenylenediamine (11) is firstly mixed with p-iodotoluene in the proportion of about 1:2 (molar ratio) and copper powder, copper oxide or copper halide is added to the mixture which is reacted in the presence of a basic substance to synthesize an intermediate compound (13).

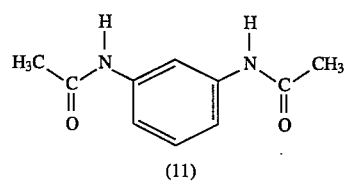
(11)

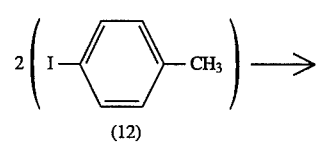
(12)

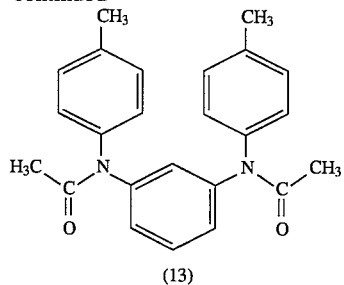

Then, a compound (14) obtained by deacetylating the resulting compound (13) is mixed with 4-isopropyliodobenzene (15) in the proportion of 1:2 (molar ratio), and the mixture was reacted according to the same manner as that described above to synthesize the objective compound (4-2).

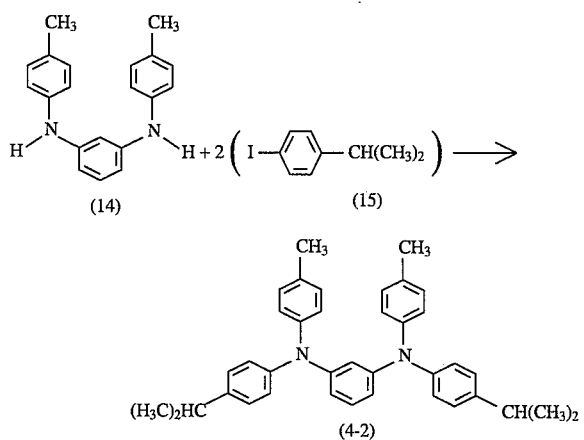

It is considered that the phenylenediamine derivative (4) has a large free volume of the molecule because of it's stereostructure, and has an elasticity to strain. When using this phenylenediamine derivative (4) as the hole transferring material in the electrophotosensitive material, a photosensitive material having an excellent wear resistance can be obtained.

Examples of the other hole transferring material in the present invention include benzidine derivatives represented by the formula (5), (6) and (7). These may be used alone or in combination thereof.

In the formulas (5) to (7), examples of the alkyl group in the substituents except the substituents $R^{18}$ and $R^{19}$ include the same substituents as those described above. The alkyl group corresponding to the substituents $R^{18}$ to $R^{19}$ may be those having 3 to 5 carbon atoms among them. Furthermore, examples of the aryl group include phenyl group, naphthyl group, anthryl group, phenanthryl group, etc.

Examples of the benzidine derivative (2) represented by the formula (5) include compounds of the following formulas (5-1) to (5-2).

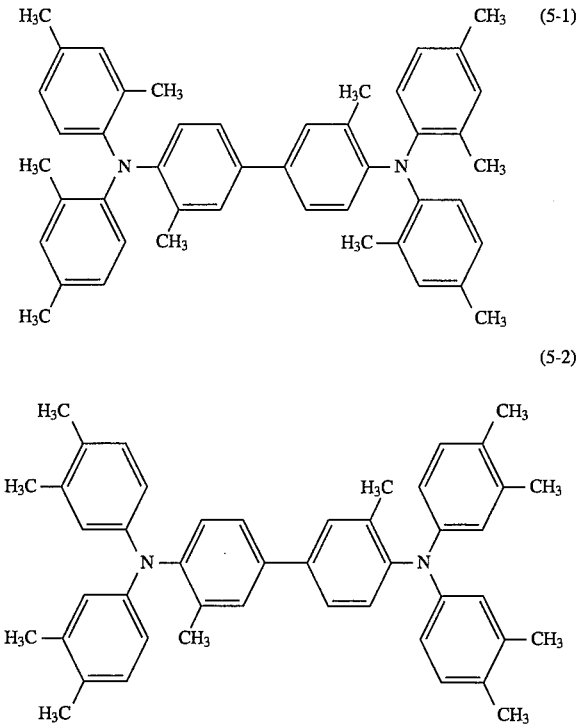

Examples of the benzidine derivative (6) include compounds of the following formulas (6-1) to (6-5).

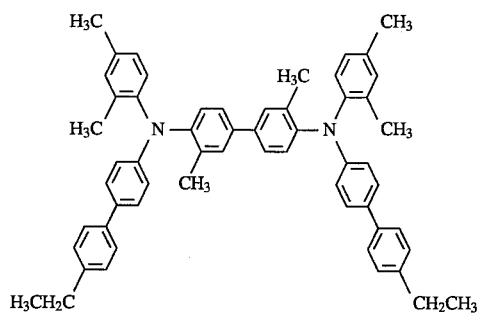

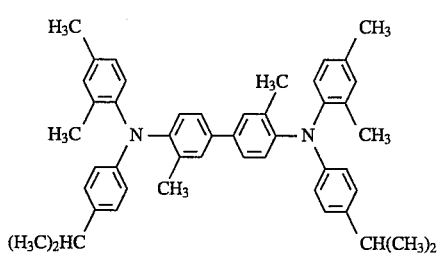

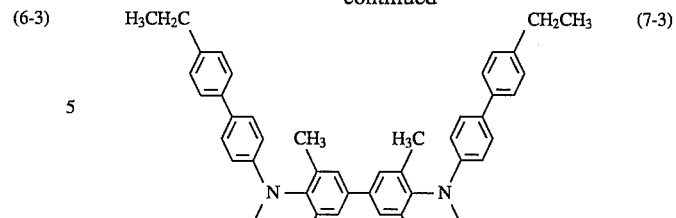

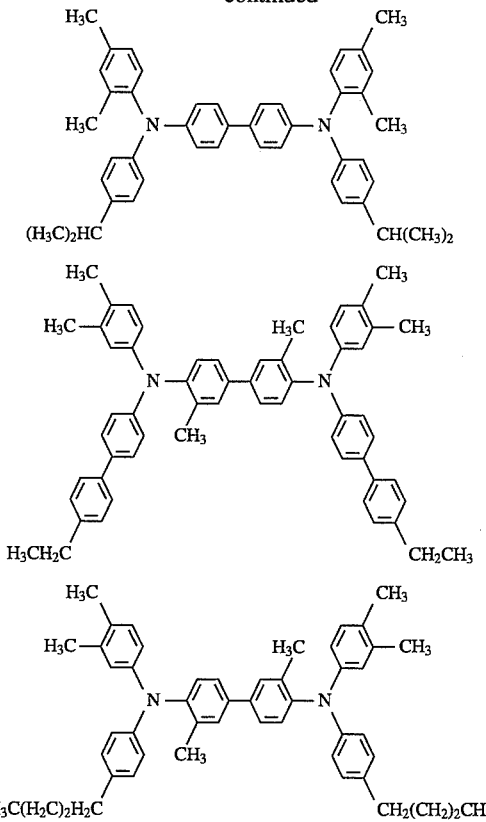

Examples of the benzidine derivative represented by the formula (7) include compounds of the following formulas (7-1) to (7-3).

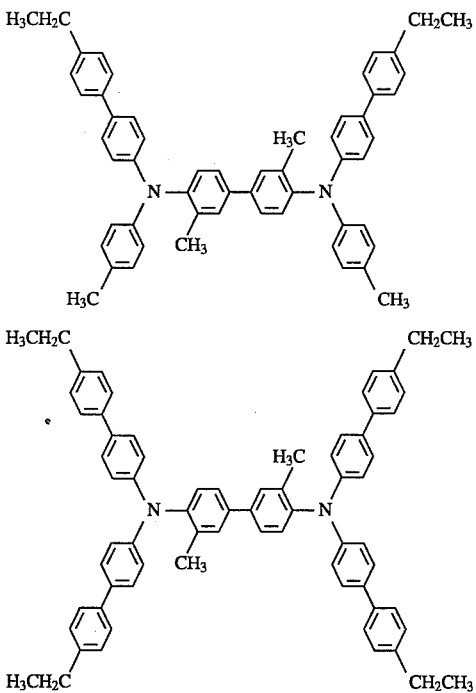

The benzidine derivatives (5), (6) and (7) can be synthesized by various methods. For example, in the synthesis of the benzidine derivative represented by the formula (6-1), N,N'-diacetyl-3,3'-dimethylbenzidine (22) is firstly mixed with 2,4-dimethyliodotoluene (23) in the proportion of about 1:2 (molar ratio) and copper powder, copper oxide or copper halide is added to the mixture which is reacted in the presence of a basic substance to synthesize an intermediate compound (24). The reaction scheme will be shown below.

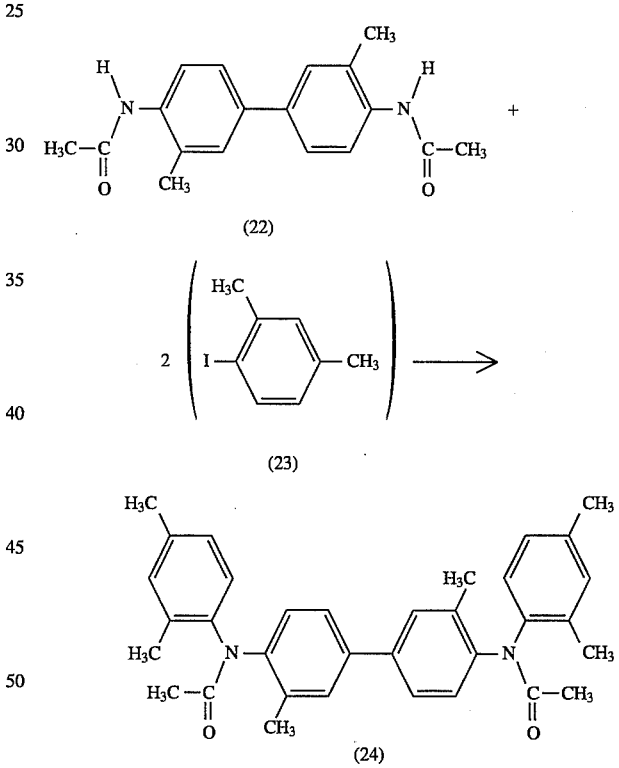

Then, the compound (24) is deacetylated and the resulting compound (25) is mixed with 4-ethyl-4'-iodobiphenyl (26) in the proportion of 1:2 (molar ratio), and the mixture was reacted according to the same manner as that described above to synthesize the objective compound (6-1). The reaction scheme will be shown below.

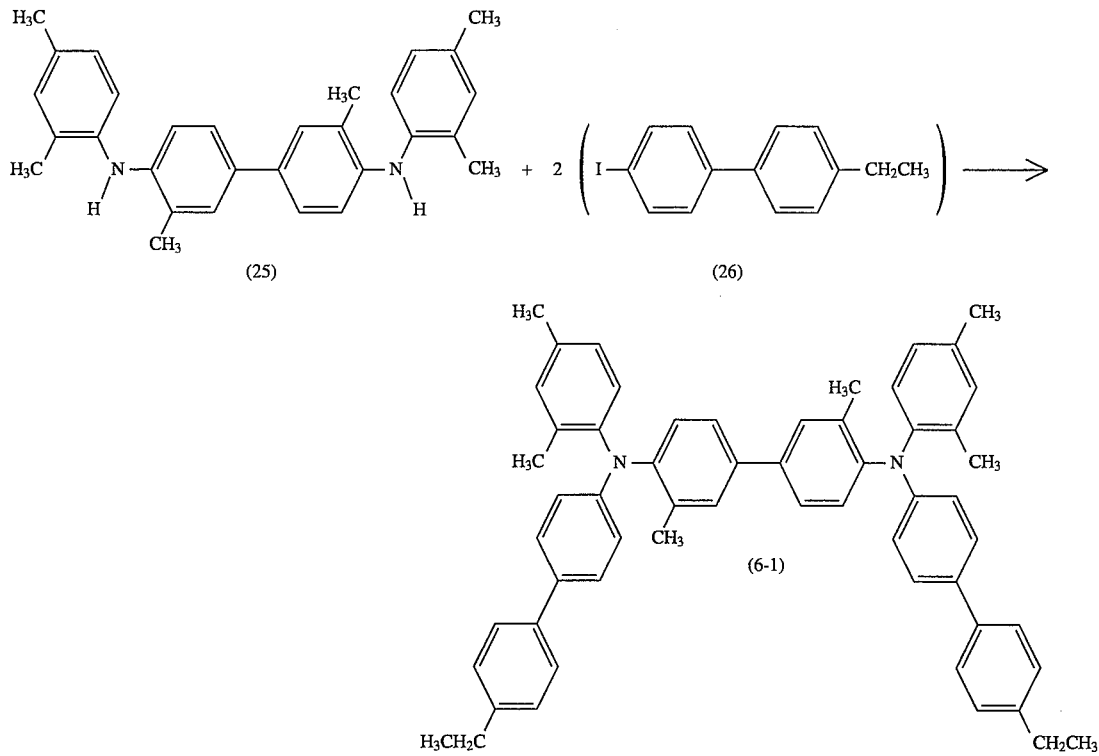

All of the benzidine derivatives (5), (6) and (7) have a high melting point (not less than 180° C.). Therefore, an electrophotosensitive material having a sufficiently high glass transition temperature can be obtained by using the benzidine derivative (5), (6) or (7) as the hole transferring material.

As the phenylenediamine derivative (4) or benzidine derivatives (5), (6) and (7) to be used as the hole transferring material, as described above, those having an ionization potential of 4.8 to 5.8 eV, particularly 5.0 to 5.6 eV may be preferably used. Further, those having an electric charge mobility of not less than $1\times10^{-6}$ cm$^2$/V second at an electric field strength of $3\times10^5$ V/cm are particularly preferred.

When the hole transferring material of the compounds of the formula (4) and/or formula (5), (6) or (7) is used in combination with the electron transferring material of the tryptoanthorine or its derivative of the formula (3), there is an extremely little fear that the above complex will be formed. However, it is possible to remove a fear of forming the complex by introducing a substituent having a volume as large as possible into the compound of the formula (3) and/or compound of the formula (4), (5), (6) or (7).

It is most effective to use the electrophotosensitive material comprising the combination of the phenylenediamine derivative (4) or benzidine derivative (5), (6) or (7) and tryptoanthorine or its derivative (3) of the present invention as the single-layer type. Such a single-layer type electrophotosensitive material is formed by providing an organic photosensitive layer on a conductive substrate, and, at least, the electric charge generating material, electron transferring material comprising the tryptoanthorine or its derivative (3), and hole transferring material comprising the phenylenediamine derivative (4) or benzidine derivative (5), (6) or (7) are contained in the binding resin in the organic photosensitive layer. In that case, the single-layer type electrophotosensitive material using the phenylenediamine derivative (4) as the hole transferring material has an excellent sensitivity and is also superior in wear resistance of the surface of the photosensitive layer. Furthermore, the electrophotosensitive material using the benzidine derivative (5), (6) or (7) as the hole transferring material has an excellent sensitivity, and the glass transition temperature of the photosensitive layer shows a sufficiently high value.

The single-layer type photosensitive material can be applied for positive charging and negative charging types, but is particularly preferred to use as the positive charging type.

When the electron accepting compound having an oxidation-reduction potential of −0.8 to −1.4 V is contained in the above single-layer type electrophotosensitive material, electrons are efficiently abstracted from the electric charge generating material, thereby further improving the sensitivity of the photosensitive material.

Furthermore, the electrophotosensitive material of the present invention can also be used as the multi-layer type. In this case, the multi-layer type photosensitive material can be applied for both positive charging and negative charging types.

In the single-layer type and multi-layer type electrophotosensitive materials, the sensitivity of the photosensitive material is improved by blending the electron accepting compound having an oxidation-reductionpotential of −0.8 to −1.4 V. The reason is considered as follows.

The electric charge generating material, which absorbed light in the exposure process, forms an ion pair, i.e. holes (+) and electrons (−). In order that this formed ion pair becomes a free carrier to cancel a surface electric charge effectively, it is preferred that there is not much possibility that the ion pair will recombine to disappear. In this case, when the electron accepting compound having an oxidation-reduction (Ox.-Red.) potential of −0.8 to −1.4 V exists, the energy level of LUMO (which means the orbital of which energy level is most low in molecular orbitals containing no electrons, and the excited electrons normally transfer to this orbital) in the electron accepting compound is lower than that of the electric charge generating material. Therefore, electrons transfer to the electron accepting compound when the ion pair is formed, and the ion pair is liable to separate into the carrier. That is, the electron accepting compound acts on the generation of electric charges to improve the electric charge generating efficiency.

Furthermore, it is also necessary to cause no carrier-trapping due to impurities at the time of transferring of the free carrier, so that the photosensitive material may have a high sensitivity. Normally, a trapping due to a small amount of impurities is caused in the transfer process of the free carrier, and the free carrier transfers while causing trapping-detrapping repeatedly. Accordingly, when the free carrier is fallen into the level where detrapping can not be effected, carrier trapping is arisen and it's transfer is stopped.

When using the electron accepting compound having an Ox-Red. potential of more than −0.8 V (i.e. having a large electron affinity), the separated free carrier is fallen into the level where detrapping can not be effected to cause carrier trapping. To the contrary, in case of the electron accepting compound having an Ox.-Red potential of less than −1.4 V, the energy level of LUMO becomes higher than that of the electric charge generating material. When the ion pair is formed, no electrons are transferred to the electron accepting compound, which fails to improve the electric charge-generating efficiency.

The Ox-Red. potential will be measured by using a three-electrode system cyclic voltametry using the following materials.

Electrode: Work electrode (glassy carbon electrode),
 Counter electrode (platinum electrode) Reference electrode (silver nitrate electrode, 0.1N $AgNO_3$—$CH_3CN$ solution)

Measuring solution:
 Solvent ($CH_2Cl_2$, 1 liter)
 Measuring substance (electron accepting compound, 0.001 mols)
 Electrolyte (tetra-n-butylammonium perchlorate, 0.1 mols)

The above materials are mixed to prepare a measuring solution.

Calculation of Ox.-Red. potential: As shown in FIG. 1, a relation between the tractive voltage (V) and current (μA) is determined to measure $E_1$ and $E_2$ shown in the same figure, then the Ox.-Red. potential is determined according to the following calculation formula:

Ox.-Red. potential=$(E_1+E_2)/2(V)$

The electron accepting compound which can be used in the present invention may be any compound having electron acceptance properties and an Ox-.Red. potential of −0.8 to −1.4 V. Non-limited examples thereof include benzoquinone compounds, naphthoquinone compounds, anthraquinone compounds (e.g. nitroanthraquinone, dinitroanthraquinone, etc.), diphenoquinone compounds, thiopyran compounds, fluorenone compounds (e.g. 3,4,5,7-tetranitro-9-fluorenone, etc.), xanthene compounds (e.g. 2,4,8-trinitrothioxanthene, etc.), dinitroanthracene, dinitroacridine, malononitrile, etc. Among them, diphenoquinone compounds are particularly preferred because a quinone oxygen atom having excellent electron acceptance properties is bonded to the molecular chain terminal and a conjugate double bond exists along the whole long molecular chain, thereby facilitating electron transfer in the molecule as well as giving and receiving of electrons between molecules. Furthermore, the above respective electron accepting compound contributes to the generation of electric charges.

Examples of the benzoquinone derivative include p-benzoquinone, 2,6-dimethyl-p-benzoquinone, 2,6-di-t-butyl-p-benzoquinone, etc.

Furthermore, the diphenoquinone compound is represented by the formula (16):

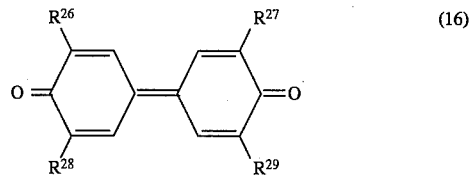

wherein $R^{26}$, $R^{27}$, $R^{28}$ and $R^{29}$ are the same or different and indicate a hydrogen atom, an alkyl group, an aryl group or an alkoxy group. Examples thereof include 3,3',5,5'-tetramethyl-4,4'-diphenoquinone, 3,3',5,5'-tetraethyl-4,4'-diphenoquinone, 3,3',5,5'-tetra-t-butyl-4,4'-diphenoquinone, 3,5-dimethyl-3',5'-di-t-butyl-4,4'-diphenoquinone, 3,3'-dimethyl-5',5'-di-t-butyl-4,4'-diphenoquinone, 3,5'-dimethyl-3',5-di-t-butyl-4,4'-diphenoquinone, etc. These diphenoquinone compounds can be used alone or in combination thereof.

The phenylenediamine derivative (4) and benzidine derivative (5), (6) or (7) in the present invention may be used alone or in combination thereof. Furthermore, they may be used in combination with the other known hole transferring material described above.

Examples of the electric charge generating material to be used in the present invention include selenium, selenium-tellurium, amorphous silicon, pyrilium salt, azo pigments, disazo pigments, anthanthrone pigments, phthalocyanine pigments, naphthalocyanine pigments, indigo pigments, triphenylmethane pigments, threne pigments, toluidine pigments, pyrazoline pigments, quinacridon pigments, dithioketopyrrolopyrrole pigments and the like. These electric charge generating materials can be used alone or in combination thereof to present an absorption wavelength within a desired range.

It is preferred in view of the reduction of the residual potential and improvement of the sensitivity to use the electric charge generating material having an ionization potential balanced with the hole transferring material, electric charge generating material having an ionization potential within a range of 4.8 to 6.0 eV, preferably 5.0 to 5.8 eV in connection with the fact that the hole transferring material having an ionization potential of 4.8 to 5.8 eV, particularly 5.0 to 5.6 eV is used.

Furthermore, examples of the electric charge generating material suitable for the organic photosensitive material to be used for a digital-optical image forming apparatus using a light source having a wavelength of not less than 700 nm include phthalocyanine pigments such as X type metal-free phthalocyanine, oxotitanylphthalocyanine, etc. Since these phthalocyanine pigments are superior in matching with the electron transferring material of the formula (3), a photosensitive material having a high sensitivity within the above wavelength range can be obtained by using them in combination. For example, the resulting photosensitive material can be suitably used for digital-optical image forming apparatuses such as laser beam printer, facsimile, etc.

On the other hand, examples of the electric charge generating material suitable for the organic photosensitive material to be used for an analog-optical image forming apparatus using a light source having a wavelength of the visible range include perylene pigments represented by the formula:

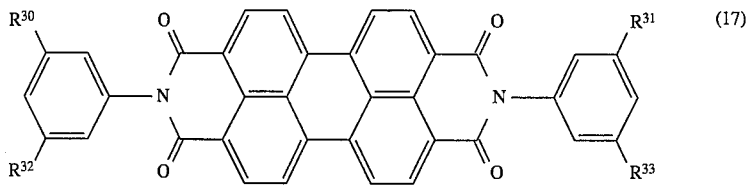

wherein $R^{30}$, $R^{31}$, $R^{32}$ and $R^{33}$ are the same or different and indicate a hydrogen atom, an alkyl group, an alkoxyl group or an aryl group. Examples of the alkyl group, alkoxy group and aryl group in the formula (17) include the same groups as those described above.

Since these perylene pigments have a sensitivity within the visible range and are superior in matching with the tryptoanthorine or its derivative of the formula (3), an electrophotosensitive material obtained by using them in combination has a high sensitivity within the visible range, and it can be suitably used for analog-optical image forming apparatuses such as electrostatic copying machine, etc.

It is preferred in view of the reduction of the residual potential and improvement of the sensitivity to use a perylene pigment having an ionization potential balanced with the hole transferring material, i.e., perylene pigment having an ionization potential within a range of 4.8 to 5.8 eV in connection with the fact that the hole transferring material having an ionization potential of 4.8 to 5.8 eV, particularly 5.0 to 5.6 eV is used.

As the binding resin for dispersing the above respective components, there can be used various resins which have hitherto been used for the organic photosensitive layer, and examples thereof include thermoplastic resins such as styrene polymer, styrene-butadiene copolymer, styreneacrylonitrile copolymer, styrene-maleic acid copolymer, acrylic copolymer, styrene-acrylic acid copolymer, polyethylene, ethylene-vinyl acetate copolymer, chlorinated polyethylene, polyvinyl chloride, polypropylene, ionomer, vinyl chloride-vinyl acetate copolymer, polyester, alkyd resin, polyamide, polyurethane, polycarbonate, polyalylate, polysulfon, diaryl phthalate resin, ketone resin, polyvinyl butyral resin, polyether resin, polyester resin, etc.; crosslinking thermosetting resins such as silicone resin, epoxy resin, phenol resin, urea resin, melamine resin, etc.; photosetting resins such as epoxy acrylate, urethane acrylate, etc. These binding resins can be used alone or in combination thereof. Suitable resins are styrene polymer, acrylic polymer, styrene-acrylic copolymer, polyester, alkyd resin, polycarbonate, polyacrylate, etc.

Further, various additives, such as deterioration inhibitors (e.g. antioxidants, radical scavengers, singlet quenchers, ultraviolet absorbers, etc.), softeners, plasticizers, surface modifiers, bulking agents, thickening agents, dispersion stabilizers, wax, acceptors, donors, etc. can be blended in the photosensitive layer without injury to the electrophotographic characteristics. The amount of these additives to be added may be the same as that used in a conventional technique. For example, a steric hindered phenolic antioxidant may be blended in an amount of about 0.1 to 50 parts by weight, based on 100 parts by weight of the binding resin.

In order to improve the sensitivity of the photosensitive layer, known sensitizers such as terphenyl, halonaphthoquinones, acenaphthylene, etc. may be used in combination with the electric charge generating material.

Furthermore, other electron transferring materials which have hitherto been known can be contained in the photosensitive layer, together with the compound represented by the formula (3). Examples of the electron transferring material include benzoquinone compounds, diphenoquinone compounds, malononitrile compounds, thiopyran compounds, tetracyanoethylene, 2,4,8-trinitrothioxanthone, fluorenone compounds (e.g. 3,4,5,7-tetranitro-9-fluorenone, etc.), dinitrobenzene, dinitroanthracene, dinitroacridine, nitroanthraquinone, dinitroanthraquinone, succinic anhydride, maleic anhydride, dibromomaleic anhydride, etc.

As the conductive substrate to be used for the photosensitive material of the present invention, various materials having a conductivity can be used, and examples thereof include metals such as aluminum, copper, tin, platinum, silver, vanadium, molybdenum, chromium, cadmium, titanium, nickel, palladium, indium, stainless steel, brass, etc.; plastic materials vapor-deposited or laminated with the above metal; glass materials coated with aluminum iodide, tin oxide, lndium oxide, etc.

The conductive substrate may be made in the form of a sheet or a drum. The substrate itself may have a conductivity or only the surface of the substrate may have a conductivity. It is preferred that the conductive substrate has a sufficient mechanical strength when used.

The photosensitive layer in the present invention is produced by applying a coating solution, which is prepared-by dissolving or dispersed a resin composition containing the above-described respective components in a solvent, on the conductive substrate, followed by drying.

The effect due to the use of the electron transferring material in the present invention can be obtained in the single-layer type photosensitive material, particularly. The single-layer type photosensitive material of the present invention can be applied to positive charging and negative charging type photosensitive materials, and it is particularly preferred to use for the positive charging type photosensitive material.

In order to obtain the single-layer type electrophotosensitive material, the predetermined electron transferring material, hole transferring material, electric charge generating material and binding resin may be dissolved or dispersed in a suitable solvent and the resulting coating solution is applied on a conductive substrate, followed by drying. Known methods (e.g. roll mill, ball mill, disper mill, atriter, paint shaker or ultrasonic dispersion device) can be used for preparing the coating solution.

In the single-layer type electrophotosensitive material, it is preferred that the electric charge generating material may be blended in the photosensitive layer in an amount of 0.5 to 50 parts by weight, preferably 0.5 to 30 parts by weight, particularly 0.5 to 5 parts by weight, based on 100 parts by weight of the binding resin. It is preferred that the hole transferring material may be blended in the photosensitive layer in an amount of 5 to 500 parts by weight, preferably 25 to 200 parts by weight, more preferably 5 to 100 parts by weight, particularly 50 to 80 parts by weight, based on 100 parts by weight of the binding resin.

It is preferred that the electron transferring material containing the tryptoanthorine or its derivative of the formula (3) may be blended in the photosensitive layer in an amount of 5 to 100 parts by weight, particularly 10 to 80 parts by weight, based on 100 parts by weight of the binding resin. Furthermore, it is suitable that the total amount of the hole transferring material and electron transferring material is 20 to 500 parts by weight, preferably 30 to 200 parts by weight, based on 100 parts by weight of the binding resin. When the electron accepting compound is blended, it is preferred to blend in an amount of 0.1 to 40 parts by weight, preferably 0.5 to 20 parts by weight, based on 100 parts by weight of the binding resin.

In the single-layer type photosensitive material, the thickness of the photosensitive layer is preferably about 5 to 50 µm, preferably 5 to 50 µm, more preferably 10 to 50 µm, particularly 10 to 40 µm.

In order to obtain the multi-layer type photosensitive material, the electric charge generating material is firstly deposited alone on a conductive substrate to form an electric charge generating layer, or an electric charge generating layer containing an electric charge generating material and a binding resin and, if necessary, a hole transferring material is formed using a means such as application, etc. Then, an electron transferring layer containing an electron transferring material and a binding resin is formed on this electric charge generating layer. On the other hand, the electric charge generating layer may be formed after the electron transferring layer was formed on the conductive substrate.

In the multi-layer photosensitive material, the electric charge generating material and the binding resin which constitute the resin dispersion type electric charge generating layer may be used in various proportions. It is preferred that the electric charge generating material may be used in an amount of 5 to 1000 parts by weight, particularly 30 to 500 parts by weight, based on 100 parts by weight of the binding resin.

The electron transferring material and binding resin which constitute the electric charge transferring layer can be used in various proportions within such a range as not to prevent the electron transfer and to prevent the crystallization. It is preferred that the electron transferring material may be used in an amount of 10 to 500 parts by weight, particularly 25 to 200 parts by weight, based on 100 parts by weight of the binding resin to easily transfer electrons generated by light irradiation in the electric charge generating layer.

Furthermore, in the multi-layer type photosensitive layer, the thickness of the electric charge generating layer is preferably about 0.01 to 5 µm, particularly about 0.1 to 3 µm, and that of the electric charge transferring layer is preferably about 2 to 100 µm, particularly about 5 to 50 µm.

A barrier layer may be formed, in such a range as not to injure the characteristics of the photosensitive material, between the conductive substrate and photosensitive layer in the single-layer type photosensitive material, or between the conductive substrate and electric charge generating layer or between the conductive substrate layer and electric charge transferring layer in the multi-layer type photosensitive material. Furthermore, a protective layer may be formed on the surface of the photosensitive layer.

When the photosensitive layer is formed by the application method, the electric charge generating material, electric charge transferring material and binding resin may be dispersed and mixed with a suitable solvent using a known method, such as roll mill, ball mill, atriter, paint shaker, ultrasonic dispersion device, etc., and the resulting solution may be applied using a known means, followed by drying.

As the solvent, there can be used various organic solvents, and examples thereof include alcohols such as methanol, ethanol, isopropanol, butanol, etc.; aliphatic hydrocarbons such as n-hexane, octane, cyclohexane, etc.; aromatic hydrocarbons such as benzene, toluene, xylene, etc.; halogenated hydrocarbons such as dichloromethane, dichloroethane, carbon tetrachloride, chlorobenzene, etc.; ethers such as dimethyl ether, diethyl ether, tetrahydrofuran, ethylene glycol dimethyl ether, diethylene glycol dimethyl ether, etc.; ketones such as acetone, methyl ethyl ketone, cyclohexanone, etc.; esters such as ethyl acetate, methyl acetate, etc.; dimethylformaldehyde, dimethylformamide, dimethyl sulfoxide, etc. These solvents may be used alone or in combination thereof.

In order to improve a dispersibility of the electric charge transferring material and electric charge generating material as well as a smoothness of the surface of the photosensitive layer, surfactants, leveling agents, etc. may be used.

As described above, since the tryptoanthorine or its derivative (3) of the present invention is superior in electron transferring capability, the electrophotosensitive material using this as the electron transferring material has a high sensitivity. Accordingly, speeding up of copying machine, printer, etc. can be attained when using the photosensitive material of the present invention.

EXAMPLES

The following Synthesis Examples, Examples and Comparative Examples further illustrate the present invention in detail.

Synthesis Example 1

[Production of 6-isopropyltryptoanthorine]

Isatoic acid anhydride (3.2 g, 21.7 mmols) and 5-isopropylisatin (3.4 g, 17.8 mmols) were dissolved in 10 ml of pyridine and, the mixture was reacted under reflux for 5 hours.

After the completion of the reaction, the crystal deposited in the reaction solution was filtered and washed with methanol, and then recrystallized from methanol to give 2.3 g (yield: 46%) of the titled compound represented by the formula:

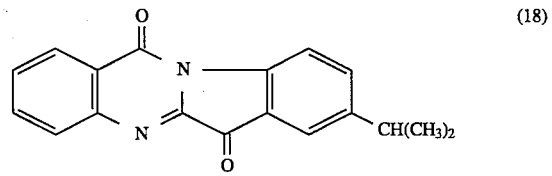

(18)

Melting point: 188° C.

Figure 2:
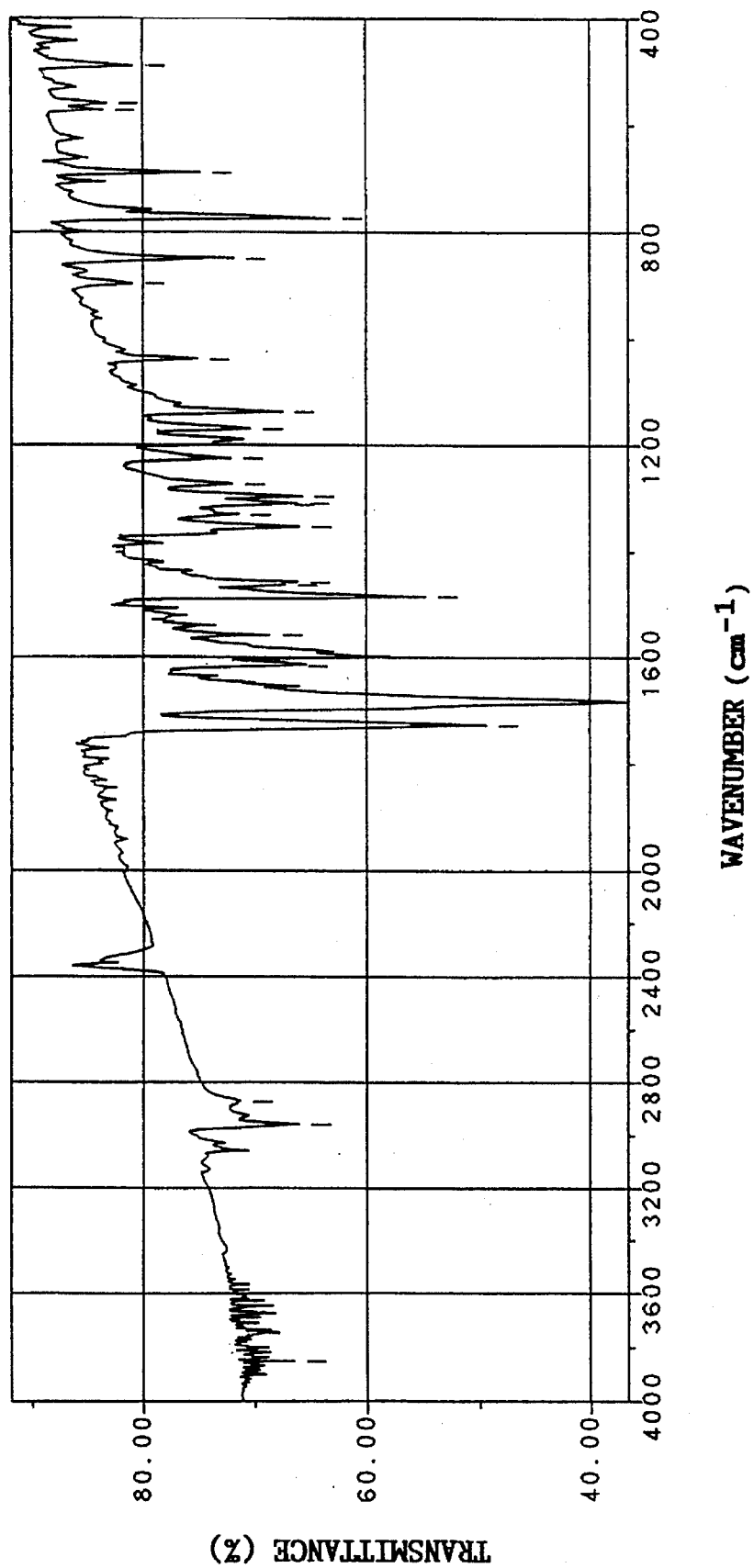
FIG. 2 is a graph illustrating an infrared absorption spectrum of the product obtained in Example 1.

An infrared absorption spectrum of this product is shown in FIG. 2.

(Evaluation of electron transferring capability)

The electron transferring capability of the compound obtained in Synthesis Example 1 was evaluated using a TOF method. As a result, it has been found that this compound shows a mobility of $8 \times 10^{-7}$ cm$^2$/V at an electric field strength of $3 \times 10^5$ V/cm and has a high electron transferring capability.

Examples 1–4

| <Components> | (parts by weight) |
|---|---|
| Electric charge generating material | 1 |
| Hole transferring material | 60 |
| Electron transferring material | 40 |
| Binding resin | 100 |
| (bisphenol Z type polycarbonate) | |

The above respective components were mixed and dispersed with a predetermined amount of dichloromethane using a ball mill to prepare a coating solution for single-layer type photosensitive layer. Then, this coating solution was applied on an aluminum foil using a wire bar, followed by hot-air drying at 100° C. for 60 minutes to give a single-layer type photosensitive material for digital light source, which has a film thickness of 15 to 20 μm.

The respective components used are as follows.
(Electron transferring material)
- (18): 6-Isopropyltryptoanthorine of the formula (18) obtained in Synthesis Example 1
- (2): Tryptoanthorine of the formula (2)

(Electric charge generating material)
- I: X type metal-free phthalocyanine (Ip=5.38 eV)
- II: Oxotitanylphthalocyanine (Ip=5.32 eV)

(Hole transferring material)
- N,N,N',N'-tetrakis(p-methylphenyl)-3,3'-dimethylbenzidine (Ip=5.56 eV)

Comparative Examples 1–2

According to the same manner as that described in Examples 1 to 4 except for using 2,6-dimethyl-2',6'-di-t-butyl-4,4'-diphenoquinone (represented by the symbol (a)) in place of 6-isopropyltryptoanthorine (18) and tryptoanthorine (2) as the electron transferring material, a single-layer type photosensitive material for digital light source was prepared.

Comparative Example 3

According to the same manner as that described in Examples 1 to 4 except for containing no electron transferring material, a single-layer type photosensitive material for digital light source was prepared.

Examples 5–6

100 Parts by weight of X type metal-free phthalocyanine and 100 parts by weight of polyvinyl butyral were mixed and dispersed with a predetermined amount of tetrahydrofuran using a ball mill to prepare a coating solution for electric charge generating layer. Then, this coating solution was applied on an aluminum foil using a wire bar, followed by hot-air drying at 100° C. for 60 minutes to form an electric charge generating layer having a film thickness of about 1 μm.

On the other hand, 100 parts by weight of 6-isopropyl-tryptoanthorine (18) or tryptoanthorine (2) obtained in Synthesis Example 1 and 100 parts by weight of a polycarbonate resin were mixed and dispersed with a predetermined amount of toluene using a ball mill to prepare a coating solution for electron transferring layer. Then, this coating solution was applied on the above electric charge generating layer using a wire bar, followed by hot-air drying at 100° C. for 60 minutes to form an electron transferring layer having a film thickness of 20 μm, thereby preparing a positive charging type multi-layer type photosensitive material for digital light source.

Comparative Example 4

According to the same manner as that described in Examples 5 and 6 except for using the same diphenoquinone derivative as that used in Comparative Examples 1 and 2 as the electron transferring material, a positive charging type multi-layer type photosensitive material for digital light source was prepared.

Evaluation of electrophotosensitive material

By using an electrostatic copying tester (EPA-8100, manufactured by Kawaguchi Denki Co., Ltd.), a voltage was applied to an electrophotosensitive material to positively charge it, and electrophotographic characteristics were determined using monochromatic light having a wavelength of 780 nm (half-width: 20 nm) from white light of a halogen lamp as a light source through a band-pass filter. The results are shown in Table 1.

"V1" in Table 1 indicates an initial surface potential of the photosensitive material when a voltage is applied to charge the photosensitive material, and "V2" indicates a residual potential obtained by measuring a surface potential at the time at which 0.8 seconds has passed since the beginning of exposure. Furthermore, "$E_{1/2}$" indicates a half-life exposure when the initial surface potential V1 is reduced to half.

In Tables to be given hereinafter, "CGM" and "ETM" denote "charge generating material" and "electron transferring material", respectively.

TABLE 1

| | CGM | ETM | V1 (V) | V2 (V) | $E_{1/2}$ (Lux · sec.) |
|---|---|---|---|---|---|
| Ex. 1 | I | (18) | +706 | +42 | 1.0 |
| Ex. 2 | II | (18) | +711 | +46 | 1.1 |
| Ex. 3 | I | (2) | +700 | +48 | 1.1 |
| Ex. 4 | II | (2) | +704 | +52 | 1.2 |
| Comp. Ex. 1 | I | (a) | +718 | +63 | 1.7 |
| Comp. Ex. 2 | II | (a) | +712 | +69 | 1.8 |
| Comp. Ex. 3 | I | — | +710 | +456 | — |
| Ex. 5 | I | (18) | +709 | +59 | 1.1 |
| Ex. 6 | I | (2) | +701 | +65 | 1.2 |
| Comp. Ex. 4 | I | (a) | +714 | +91 | 2.4 |

As is apparent from the results of Table 1, all of photosensitive materials of Examples 1 to 6 of the present invention have a high sensitivity in comparison with the corresponding Comparative Examples because the residual potential (V1) and half-life exposure (E1/2) are decreased.

Furthermore, as is apparent from the comparison between the respective Examples, the Example using the tryptoanthorine derivative (18) has a high sensitivity in comparison with that using tryptoanthorine (2) because the residual potential (V1) and half-life exposure (V2) are decreased.

Synthesis Example 2

(Production of 2,6-diethyltryptoanthorine)

(i) Chloral hydrate (26 g), water (324 g) and anhydrous sodium sulfate (171 g) were charged in a 1 liter egg-plant type flask, and the mixture was stirred at 40° to 50° C. To the mixture, a solution obtained by adding p-ethylaniline (14.7 g) to 100 ml of an aqueous 10% hydrochloric acid was added and hydroxylammonium chloride (22.5 g) was further added, and the mixed solution was refluxed for 30 minutes. After ice cooling, the deposit was filtered and washed three times with water, and then recrystallized from ethanol to give a reaction product.

Concentrated sulfuric acid (200 ml) was charged in another 500 ml two-neck flask, followed by ice cooling. Then, the above reaction product (62.9 g) was gradually added and the mixture was stirred with ice cooling for 30 minutes. After stirring at 70° to 75° C. for additional 10 minutes, the reaction solution was cooled and poured into ice. The deposit was filtered and the solid was recrystallized from methanol to give 17.8 g (yield: 53.5%) of an isatin derivative represented by the following formula (19):

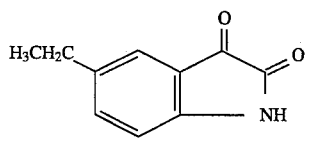

(19)

(ii) The isatin derivative (70 g) obtained in the above item (i), 200 ml of acetic acid and 0.8 ml of concentrated sulfuric acid were charged in a 500 ml two-neck flask and the mixture was stirred at room temperature. Then, 50 ml of 30% hydrogen peroxide was added dropwise to the mixture. After the completion of dropping, the mixture was stirred at 60° to 65° C. for one hour and a half and then cooled. The deposit was filtered, washed with water and dried under vacuum to give 35 g of a derivative of isatoic acid anhydride represented by the following formula (20):

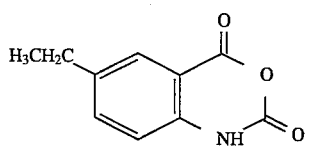

(20)

(iii) The derivative of isatoic acid anhydride (10 g) obtained in the above item (ii), the isatin derivative (10 g) obtained in the above item (i) and 10 ml of pyridine were charged in a 200 ml flask, and the mixture was refluxed. After the reaction solution was cooled, the deposit was filtered and dissolved in chloroform. Then, the solution was washed with water and dried over anhydrous sodium sulfate. After the solvent was removed, 5.2 g of the titled compound represented by the formula:

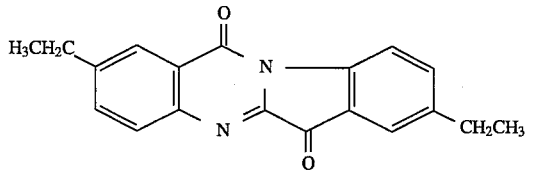

(21)

as a yellow solid.
Melting point: 184° C.

Example 7

According to the same manner as that described in Example 1 except for using the tryptoanthorine derivative (21) obtained in Synthesis Example 2 in place of the tryptoanthorine derivative used in the Example 1, an electrophotosensitive material was obtained. The photosensitive material of Example 7 showed +708 V of VI, +43 V of V2 and 1.0 Lux.second of $E_{1/2}$. Accordingly, the sensitivity was improved in comparison with Comparative Example 1.

Examples 8 to 19

| <Components> | (parts by weight) |
|---|---|
| Electric charge generating material | 5 |
| Hole transferring material | 50 |
| Electron transferring material | 30 |
| Binding resin | 100 |
| (bisphenol Z type polycarbonate) | |
| Solvent (tetrahydrofuran) | 800 |

The above respective components were mixed and dispersed in a ball mill for 50 hours to prepare a coating solution for single-layer type photosensitive layer. Then, this coating solution was applied on the surface of an aluminum tube as the conductive substrate using a dip coating method, followed by hot-air drying at 100° C. for 60 minutes to make an electrophotosensitive material having a single-layer type photosensitive layer of 15 to 20 μm in film thickness.

As the electric charge generating material, X type metal-free phthalocyanine (Ip=5.38 eV) was used. As the hole transferring material, any one of phenylenediamine derivatives represented by the formulas (4-1) to (4-6) was used. As the electron transferring material, the tryptoanthorine derivative represented by the formula (2) or (18) was used.

The ionization potential of the phenylenediamine derivatives represented by the formulas (4-1) to (4-6) are as follows.

(4-1)=5.62 eV, (4-2)=5.62 eV
(4-3)=5.49 eV, (4-4)=5.60 eV
(4-5)=5.58 eV, (4-6)=5.64 eV

The ionization potential (Ip) of the electric charge generating material and hole transferring material was measured in air using a photoelectron analytical apparatus (AC-1, manufactured by Riken Kiki Co., Ltd.).

Comparative Example 5

According to the same manner as that described in Examples 8 to 19 except that N,N,N',N'-tetrakis(4-methylphenyl)-3,3'-dimethylbenzidine (Ip=5.5 eV, represented by "6Me-4PhB" in Table 2) was used as the hole transferring material and 3,5-dimethyl-3',5'-di-t-butyl-4,4'-diphenoquinone (represented by "(a)" in Table 2) was used as the electron transferring material, a single-layer type electrophotosensitive material was prepared.

The resulting photosensitive materials were subjected to the following tests.

Evaluation of electrophotosensitive material

By using a drum sensitivity tester manufactured by GENTEC. Co., a voltage was applied on the surface of the photosensitive materials obtained in Example 7 and Comparative Example 5 to charge the surface at +700 V. Then, monochromatic light [wavelength: 780 nm (half-width: 20 nm), light intensity: 16 μW/cm²] from white light of a halogen lamp as an exposure light source through a band-pass filter was irradiated on the surface of the photosensitive material (irradiation time: 80 msec.). Furthermore, a surface potential at the time at which 330 msec. has passed since the beginning of exposure was measured as a potential after exposure $V_L$ (V). The smaller the potential after exposure $V_L$ is, the higher the sensitivity of the electrophotosensitive material.

Evaluation of wear resistance

A photosensitive material obtained in the respective Examples and Comparative Examples was fit with a photosensitive material drum of a facsimile ("LDC-650", manufactured by Mita Kogyo Co., Ltd.) and, after rotating 150,000 times without passing a paper through it, a change in thickness of a photosensitive layer before and after rotation was determined, respectively. The smaller the change in thickness is, the better the wear resistance.

These results are shown in Table 2, together with the hole transferring materials and electron transferring materials used. Furthermore, in order to examine the effect due to different hole transferring materials, the test was conducted using the photosensitive materials obtained in Examples 1 and 3 according to the same manner as that described above. The results are also shown in Table 2.

In Tables to be given hereinafter, "HTM" denotes "hole transffering material."

TABLE 2

|        | HTM      | ETM  | $V_L$ (V) | Amount of wear (μm) |
|--------|----------|------|-----------|---------------------|
| Ex. 8  | 4-1      | (2)  | 195       | 3.1                 |
| Ex. 9  | 4-2      | (2)  | 198       | 2.9                 |
| Ex. 10 | 4-3      | (2)  | 196       | 2.9                 |
| Ex. 11 | 4-4      | (2)  | 208       | 2.8                 |
| Ex. 12 | 4-5      | (2)  | 205       | 3.2                 |
| Ex. 13 | 4-6      | (2)  | 200       | 3.0                 |
| Ex. 14 | 4-1      | (18) | 206       | 3.1                 |
| Ex. 15 | 4-2      | (18) | 199       | 2.8                 |
| Ex. 16 | 4-3      | (18) | 194       | 2.6                 |
| Ex. 17 | 4-4      | (18) | 195       | 3.0                 |
| Ex. 18 | 4-5      | (18) | 198       | 3.1                 |
| Ex. 19 | 4-6      | (18) | 197       | 2.9                 |
| Ex. 3  | 6Me-4PhB | (2)  | 205       | 5.0                 |
| Ex. 1  | 6Me-4PhB | (18) | 199       | 5.1                 |
| Comp. Ex. 5 | 6Me-4PhB | (a) | 220    | 4.9                 |

As is apparent from Table 2, the photosensitive materials of Examples 8 to 19 have a high sensitivity because the potential after exposure $V_L$ is decreased in comparison with the photosensitive material of Comparative Example 6. with the photosensitive material of Comparative Example 6. Furthermore, the amount of wear is small and, therefore, they are superior in wear resistance. On the other hand, the potentials after exposure $V_L$ is almost the same as that of Examples 1 and 3, but the wear resistance is improved in Examples 8 to 19.

Examples 20 and 21

According to the same manner as that described in Examples 8 to 19 except that oxotitanylphthalocyanine (Ip=5.32 eV) was used as the electric charge generating material and the phenylenediamine derivative represented by the formula (4-1) was used as the hole transferring material and, further, the tryptoanthorine derivative represented by the formula (2) or (18) was used as the electron transferring material, a single-layer type electrophotosensitive material was prepared.

Comparative Example 6

According to the same manner as that described in Examples 20 and 21 except that N,N,N',N'-tetrakis(4-methylphenyl)-3,3'-dimethylbenzidine (6Me-4PhB) was used as the hole transferring material and 3,5-dimethyl-3',5'-di-t-butyl-4,4'-diphenoquinone (represented by the symbol "(a)" in Table 3) was used as the electron transferring material, a single-layer type electrophotosensitive material was pepared.

According to the same manner as that described in Examples 8 to 19, the potential after exposure $V_L$ and wear resistance were evaluated as to the resulting photosensitive materials. These results are shown in Table 3, together with the hole transferring materials and electron transferring materials used. Furthermore, in order to examine the effect due to different hole transferring materials, the test was conducted using the photosensitive materials obtained in Examples 2 and 4 according to the same manner as that described above. The test results are also shown in Table 3

TABLE 3

|            | HTM      | ETM  | $V_L$ (V) | Amount of wear (μm) |
|------------|----------|------|-----------|---------------------|
| Ex. 20     | 4-1      | (2)  | 200       | 3.0                 |
| Ex. 21     | 4-1      | (18) | 206       | 3.2                 |
| Ex. 4      | 6Me-4PhB | (2)  | 219       | 4.7                 |
| Ex. 2      | 6Me-4PhB | (18) | 211       | 4.7                 |
| Comp. Ex. 6| 6Me-4PhB | (a)  | 242       | 5.5                 |

Examples 22–27

| <Components> | (parts by weight) |
|--------------|-------------------|
| Electric charge generating material | 5 |
| Hole transferring material | 50 |
| Electron transferring material | 30 |
| Electron accepting compound | 10 |
| Binding resin (bisphenol Z type polycarbonate) | 100 |
| Solvent (tetrahydrofuran) | 800 |

A predetermined amount of the above respective components were mixed and dispersed in a ball mill for 50 hours to prepare a coating solution for single-layer type photosensitive layer. Then, a single-layer type electrophotosensitive material was prepared using the above coating solution according to the same manner as that described in Examples 8 to 19.

As the electric charge generating material, X type metal-free phthalocyanine was used. As the hole transferring material, the phenylenediamine derivative represented by the formula (4-2) or (4-6) was used. As the electron transferring material, tryptoanthorine represented by the formula (2) was used. Furthermore, as the electron accepting compound, the following compounds represented by the symbols (a) to (c) were used.

(a): 3,5-Dimethyl-3',5'-di-t-butyl-4,4'-diphenoquinone (Ox.-Red. potential: –0.86 V)

(b): 3,3',5,5'-Tetra-t-butyl-4,4'-diphenoquinone (Ox.-Red. potential: –0.94 V)

(c): 2,6-Di-t-butyl-p-benzoquinone (Ox.-Red. potential: –1.30 V)

According to the same manner as that described in Examples 8 to 19, the potential after exposure $V_L$ and wear resistance were evaluated as to the resulting photosensitive materials. The test results are shown in Table 4, together with the hole transferring materials, electron transferring materials and electron accepting materials used.

In Tables to be given hereinafter, "EAC" denotes "electron accepting compound."

TABLE 4

|        | HTM | ETM | EAC | $V_L$ (V) | Amount of wear (μm) |
|--------|-----|-----|-----|-----------|---------------------|
| Ex. 22 | 4-2 | (2) | (b) | 158       | 3.0                 |
| Ex. 23 | 4-2 | (2) | (a) | 168       | 2.9                 |
| Ex. 24 | 4-2 | (2) | (c) | 178       | 3.2                 |
| Ex. 25 | 4-6 | (2) | (b) | 160       | 3.1                 |
| Ex. 26 | 4-6 | (2) | (a) | 171       | 3.0                 |
| Ex. 27 | 4-6 | (2) | (c) | 182       | 2.9                 |

As is apparent from Table 4, the sensitivity is extremely improved, particularly, by adding an electron accepting compound having a specific Ox.-Red. potential to the photosensitive layer.

| <Components> | (parts by weight) |
|---|---|
| Electric charge generating material | 5 |
| Hole transferring material | 50 |
| Electron transferring material | 30 |
| Binding resin<br>(bisphenol Z type polycarbonate) | 100 |
| Solvent (tetrahydrofuran) | 800 |

A predetermined amount of the above respective components were mixed and dispersed in a ball mill for 50 hours to prepare a coating solution for single-layer type photosensitive layer. Then, a this coating solution was applied on the surface of an aluminum tube as the conductive substrate using a dip coating method, followed by hot-air drying at 100° C. for 60 minutes to obtain an electrophotosensitive material having a single-layer type photosensitive layer of 15 to 20 μm in film thickness.

The respective components used are as follows.

Electric charge generating material

I: X type metal-free phthalocyanine (Ip=5.38 eV)

II: Oxotitanylphthalocyanine (Ip=5.32 eV) (Hole transferring material)

(5-1): Benzidine derivative represented by the formula (5-1) (Melting point: 239.9° C., Ip=5.48 eV)

(5-2): Benzidine derivative represented by the formula (5-2) (Melting point: 217.8° C., Ip=5.51 eV)

Electron transferring material (2): Tryptoanthorine of the formula (2)

(18): Tryptoanthorine derivative of the formula (18)

The ionization potential (Ip) of the electric charge generating material and hole transferring material was measured according to the same manner as that described above.

As to the resulting photosensitive material, the sensitivity was evaluated by measuring the potential after exposure $V_L$ (V) according to the same manner as that described in Examples 8 to 19. Furthermore, the glass transition point and high-temperature storage characteristics were evaluated.

Measurement of glass transition point

About 5 mg of a photosensitive layer of the photosensitive material obtained in the above respective Examples and Comparative Examples was peeled off and put in an aluminum pan, followed by sealing to prepare a sample, respectively. Then, a glass transition temperature [Tig (extrapolated glass transition initiation temperature), JIS K 7121] of this sample was measured under the following condition using a differential scanning calorimeter [Model DSC8230D, manufactured by Rikagaku Denki Co., Ltd.].

(Measuring condition)

Environmental gas: Air

Heating rate: 20° C./minutes

Evaluation of high-temperature storage characteristics

A photosensitive material obtained in the respective Examples and Comparative Examples was fit with an imaging unit of a facsimile ("LDC-650", manufactured by Mita Industrial Co., Ltd.) and, after storing at 50° C. for 10 days, an impression formed on the surface of the photosensitive layer was measured using a surface shape tester (SE-3H, manufactured by Kosaka Kenkyusho). The smaller the impression on the surface of the photosensitive layer is, the better the high-temperature storage characteristics.

The imaging unit always make a drum keep in contact with a cleaning blade under linear pressure of 1.5 g/mm. Accordingly, when using a photosensitive material drum wherein high-temperature storage characteristics (heat resistance) is poor, the impression was formed on the surface of the photosensitive layer after use. Incidentally, when the measured value of the impression is less than 0.3 μm, it can be said that no impression was observed, because the surface roughness of the photosensitive layer is normally about 0.5μ.

These results are shown in Table 5, together with the kind of electric charge generating material, hole transferring material and electron transferring material used.

TABLE 5

| | CGM | HTM | ETM | $V_L$ (V) | Tig (°C.) | Impression (μm) |
|---|---|---|---|---|---|---|
| Ex. 28 | I | 5-1 | 2 | 201 | 76.9 | <0.3 |
| Ex. 29 | I | 5-2 | 2 | 206 | 78.0 | <0.3 |
| Ex. 30 | I | 5-1 | (18) | 198 | 77.6 | <0.3 |
| Ex. 31 | I | 5-2 | (18) | 195 | 79.0 | <0.3 |
| Ex. 32 | II | 5-1 | (2) | 208 | 78.5 | <0.3 |
| Ex. 33 | II | 5-1 | (18) | 205 | 78.3 | <0.3 |

Examples 34–45

According to the same manner as that described in Examples 28 to 33 except that the following benzidine derivatives represented by the formulas (6-1) to (6-5) were used as the hole transferring material and the electric charge generating materials and electron transferring materials shown in Table 6 were used in combination, a single-layer type electrophotosensitive material was prepared.

(6-1): Benzidine derivative of the formula (6-1) (Melting point: 204.4° C., Ip=5.51 eV)

(6-2): Benzidine derivative of the formula (6-2) (Melting point: 182.6° C., Ip=5.40 eV)

(6-3): Benzidine derivative of the formula (6-3) (Melting point: 187.6° C., Ip=5.14 eV)

(6-4): Benzidine derivative of the formula (6-4) (Melting point: 236.3° C., Ip=5.54 eV)

(6-5): Benzidine derivative of the formula (6-5) (Melting point: 180.6° C., Ip=5.53 eV)

Incidentally, the ionization potential (Ip) was measured according to the same manner as that described above.

The evaluation results of the photosensitive materials obtained in the above respective Examples are shown in Table 6, together with the kind of the electric charge generating material, hole transferring material and electron transferring material used. Incidentally, the symbols of the electric charge generating material and electron transferring material are the same as those described above.

TABLE 6

| | CGM | HTM | ETM | $V_L$ (v) | Tig (°C.) | Impression (μm) |
|---|---|---|---|---|---|---|
| Ex. 34 | I | 6-1 | (2) | 202 | 77.1 | <0.3 |
| Ex. 35 | I | 6-2 | (2) | 200 | 78.8 | <0.3 |
| Ex. 36 | I | 6-3 | (2) | 196 | 78.1 | <0.3 |
| Ex. 37 | I | 6-4 | (2) | 203 | 78.2 | <0.3 |
| Ex. 38 | I | 6-5 | (2) | 205 | 77.9 | <0.3 |
| Ex. 39 | I | 6-1 | (18) | 199 | 78.0 | <0.3 |
| Ex. 40 | I | 6-2 | (18) | 196 | 78.1 | <0.3 |
| Ex. 41 | I | 6-3 | (18) | 200 | 77.7 | <0.3 |
| Ex. 42 | I | 6-4 | (18) | 203 | 78.9 | <0.3 |
| Ex. 43 | I | 6-5 | (18) | 196 | 78.8 | <0.3 |
| Ex. 44 | II | 6-1 | (2) | 210 | 78.4 | <0.3 |
| Ex. 45 | II | 6-1 | (18) | 207 | 77.9 | <0.3 |

Examples 46–53

According to the same manner as that described in Examples 28 to 33 except that the following benzidine derivatives represented by the formulas (7-1) to (7-3) were used as the hole transferring material and the electric charge generating materials and electron transferring materials shown in Table 7 were used in combination, a single-layer type electrophotosensitive material was prepared.

(7-1): Benzidine derivative of the formula (7-1) (Melting point: 183.0° C., Ip=5.54 eV)

(7-2): Benzidine derivative of the formula (7-2) (Melting point: 270.4° C., Ip=5.55 eV)

(7-3): Benzidine derivative of the formula (7-3) (Melting point: 181.6° C., Ip=5.68 eV)

Incidentally, the ionization potential (Ip) was measured according to the same manner as that described above.

The evaluation results of the photosensitive materials obtained in the above respective Examples are shown in Table 7, together with the kind of the electric charge generating material, hole transferring material and electron transferring material used. Incidentally, the symbols of the electric charge generating material and electron transferring material are the same as those described above.

TABLE 7

| | CGM | HTM | ETM | $V_L$ (V) | Tig (°C.) | Impression (μm) |
|---|---|---|---|---|---|---|
| Ex. 46 | I | 7-1 | (2) | 198 | 77.1 | <0.3 |
| Ex. 47 | I | 7-2 | (2) | 202 | 77.4 | <0.3 |
| Ex. 48 | I | 7-3 | (2) | 199 | 78.2 | <0.3 |
| Ex. 49 | I | 7-1 | (18) | 206 | 78.0 | <0.3 |
| Ex. 50 | I | 7-2 | (18) | 203 | 78.0 | <0.3 |
| Ex. 51 | I | 7-3 | (18) | 204 | 77.7 | <0.3 |
| Ex. 52 | II | 7-1 | (2) | 207 | 77.2 | <0.3 |
| Ex. 53 | II | 7-1 | (18) | 209 | 77.4 | <0.3 |

Comparative Examples 7–12

According to the same manner as that described in Examples 28 to 33 except that the following compounds were used as the hole transferring material and electron transferring material and the electric charge generating materials shown in Table 8 were used in combination, a single-layer type photosensitive material was produced.
Hole transferring material 6Me-4PhB: N,N,N',N'-tetrakis(4-methylphenyl)-3,3'-dimethylbenzidine (melting point=172.4° C., Ip=5.54 eV)

(Electron transferring material)

(2): Tryptoanthorine of the formula (2)

(18): Tryptoanthorine derivative of the formula (18)

(a): 3,5-Dimethyl-3',5'-di-t-butyl-4,4'-diphenoquinone

Incidentally, the ionization potential (Ip) was measured according to the same manner as that described above.

The evaluation results of the photosensitive materials obtained in the above respective Comparative Examples are shown in Table 8, together with the kind of the electric charge generating material, hole transferring material and electron transferring material used. Incidentally, the symbols of the electric charge generating material are the same as those described above.

TABLE 8

| | CGM | HTM | ETM | $V_L$ (V) | Tig (°C.) | Impression (μm) |
|---|---|---|---|---|---|---|
| Comp. Ex. 7 | I | 6Me-4PhB | (2) | 205 | 69.8 | 1.3 |
| Comp. Ex. 8 | I | 6Me-4PhB | (18) | 199 | 70.0 | 1.0 |
| Comp. Ex. 9 | I | 6Me-4PhB | (a) | 220 | 69.0 | 1.2 |
| Comp. Ex. 10 | II | 6Me-4PhB | (2) | 219 | 71.0 | 1.0 |
| Comp. Ex. 11 | II | 6Me-4PhB | (18) | 211 | 69.8 | 1.1 |
| Comp. Ex. 12 | II | 6Me-4PhB | (a) | 242 | 69.1 | 1.2 |

Examples 54–59

According to the same manner as that described in Examples 22 to 27 except for using the benzidine derivative represented by the formula (5-1) as the hole transferring material, a single-layer type photosensitive material was prepared. That is, as the electric charge generating material, X type metal-free phthalocyanine was used. As the hole transferring material, the benzidine derivative represented by the formula (5-1) was used. As the electron transferring material, tryptoanthorine represented by the formula (2) or the tryptoanthorine derivative represented by the formula (18) was used. Furthermore, as the electron accepting compound, the compounds represented by the symbols (a) to (c), which were shown in Examples 22 to 27, were used.

According to the same manner as that described in Examples 28 to 33, the potential after exposure $V_L$ (V), glass transition temperature point and high-temperature storage characteristics were evaluated as to the resulting photosensitive materials. The results are shown in Table 9, together with the hole transferring materials, electron transferring materials and electron accepting materials used.

TABLE 9

| | HTM | ETM | EAC | $V_L$ (V) | Tig (°C.) | Impression (μm) |
|---|---|---|---|---|---|---|
| Ex. 54 | 5-1 | (2) | (b) | 161 | 76.7 | <0.3 |
| Ex. 55 | 5-1 | (2) | (a) | 170 | 76.8 | <0.3 |
| Ex. 56 | 5-1 | (2) | (c) | 192 | 75.3 | <0.3 |
| Ex. 57 | 5-1 | (18) | (b) | 158 | 77.7 | <0.3 |
| Ex. 58 | 5-1 | (18) | (a) | 169 | 77.4 | <0.3 |
| Ex. 59 | 5-1 | (18) | (c) | 182 | 76.0 | <0.3 |

Examples 60–65

According to the same manner as that described in Examples 54 to 59 except that the benzidine derivative represented by the formula (6-1) or (6-3) was used as the hole transferring material and the tryptoanthorine derivative represented by the formula (2) was used as the electron transferring material, a single-layer type electrophotosensitive material was prepared.

According to the same manner as that described in Examples 28 to 33, the potential after exposure $V_L$ (V), glass transition temperature point and high-temperature storage characteristics were evaluated as to the resulting photosensitive materials. The results are shown in Table 10, together with the hole transferring materials, electron transferring materials and electron accepting materials used.

TABLE 10

| | HTM | ETM | EAC | $V_L$ (V) | Tig (°C.) | Impression (μm) |
|---|---|---|---|---|---|---|
| Ex. 60 | 6-1 | (2) | (b) | 164 | 77.2 | <0.3 |
| Ex. 61 | 6-1 | (2) | (a) | 174 | 76.9 | <0.3 |
| Ex. 62 | 6-1 | (2) | (c) | 182 | 75.8 | <0.3 |
| Ex. 63 | 6-3 | (2) | (b) | 159 | 78.3 | <0.3 |
| Ex. 64 | 6-3 | (2) | (a) | 167 | 77.5 | <0.3 |
| Ex. 65 | 6-3 | (2) | (c) | 178 | 76.0 | <0.3 |

Examples 66–71

According to the same manner as that described in Examples 54 to 59 except that the benzidine derivative represented by the formula (7-1) or (7-3) was used as the hole transferring material and the tryptoanthorine derivative represented by the formula (2) was used as the electron transferring material, a single-layer type electrophotosensitive material was prepared.

According to the same manner as that described in Examples 28 to 33, the potential after exposure $V_L$ (V), glass transition temperature point and high-temperature storage characteristics were evaluated as to the resulting photosensitive materials. The results are shown in Table 11, together with the hole transferring materials, electron transferring materials and electron accepting materials used.

TABLE 11

| | HTM | ETM | EAC | $V_L$ (V) | Tig (°C.) | Impression (μm) |
|---|---|---|---|---|---|---|
| Ex. 66 | 7-1 | (2) | (b) | 160 | 77.0 | <0.3 |
| Ex. 67 | 7-1 | (2) | (a) | 168 | 76.8 | <0.3 |
| Ex. 68 | 7-1 | (2) | (c) | 180 | 75.9 | <0.3 |
| Ex. 69 | 7-3 | (2) | (b) | 162 | 78.0 | <0.3 |
| Ex. 70 | 7-3 | (2) | (a) | 172 | 77.5 | <0.3 |
| Ex. 71 | 7-3 | (2) | (c) | 179 | 76.7 | <0.3 |

As is apparent from these results, the photosensitive materials of the Examples have a high sensitivity because the potential after exposure $V_L$ is decreased in comparison with those of the corresponding Comparative Examples. Furthermore, the glass transition temperature (Tig) is high and, therefore, they are also superior in high-temperature storage characteristics.

What is claimed is:

1. An electrophotosensitive material comprising a conductive substrate and an organic photosensitive layer provided on the conductive substrate, the organic photosensitive layer containing tryptoanthorine or a derivative thereof represented by the formula:

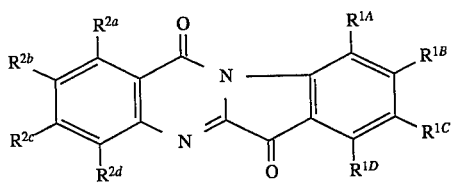

wherein $R^{1A}$, $R^{1B}$, $R^{1C}$, $R^{1D}$, $R^{2a}$, $R^{2b}$, $R^{2c}$, and $R^{2d}$ are the same or different and indicate a hydrogen atom, an alkyl group or a halogenated alkyl group.

2. The electrophotosensitive material according to claim 1, wherein the organic photosensitive layer comprises a binding resin, an electric charge generating material, an electron transferring material of tryptoanthorine represented by the formula (3) or a derivative thereof and a hole transferring material of a phenylenediamine derivative represented by the formula:

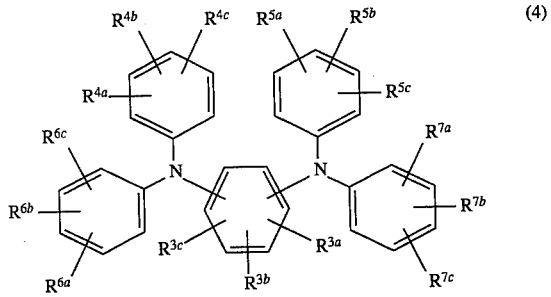

wherein $R^{3a}$, $R^{3b}$, $R^{3c}$, $R^{4a}$, $R^{4b}$, $R^{4c}$, $R^{5a}$, $R^{5b}$, $R^{5cl}$, $R^{6a}$, $R^{6b}$, $R^{6c}$, $R^{7a}$, $R^{7b}$ and $R^{7c}$ are the same or different and indicate a hydrogen atom, an alkyl group, aryl an group which may have a substituent, an alkoxy group or a halogenated alkoxy group.

3. The electrophotosensitive material according to claim 2, wherein the organic photosensitive layer further contains an electron accepting compound having an oxidation-reduction potential of –0.8 to –1.4 V.

4. The electrophotosensitive material according to claim 2, wherein the electric charge generating material is a phthalocyanine pigment.

5. The electrophotosensitive material according to claim 1, wherein the organic photosensitive layer comprises a binding resin, an electric charge generating material, an electron transferring material of a tryptoanthorine derivative represented by the formula (3) and at least one hole transferring material selected from the group consisting of benzidine derivatives represented by the following formula:

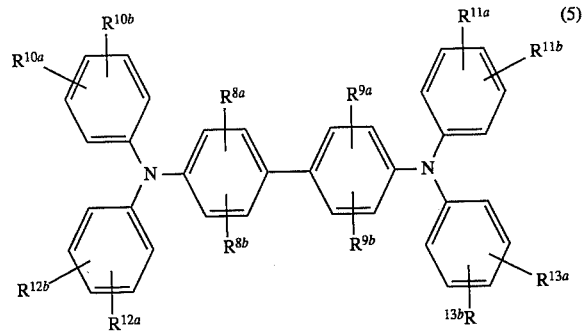

wherein $R^{8a}$, $R^{8b}$, $R^{9a}$ and $R^{9b}$ are the same or different and indicate a hydrogen atom or an alkyl group; and $R^{10a}$, $R^{10b}$, $R^{11a}$, $R^{11b}$, $R^{12a}$, $R^{12b}$, $R^{13a}$ and $R^{13b}$ are the same or different and indicate an alkyl group,

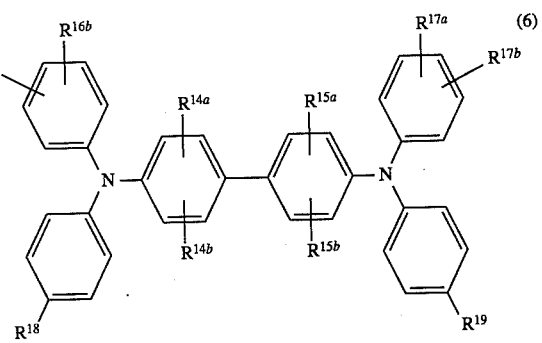

wherein $R^{14a}$, $R^{14b}$, $R^{15a}$ and $R^{15b}$ are the same or different and indicate a hydrogen atom or an alkyl group, $R^{16a}$, $R^{16b}$, $R^{17a}$ and $R^{17b}$ are the same or different and indicate an alkyl group, and $R^{18}$ and $R^{19}$ are the same or different and indicate an alkyl group having 3 to 5 carbon atoms or an aryl group which may have a substituent, and

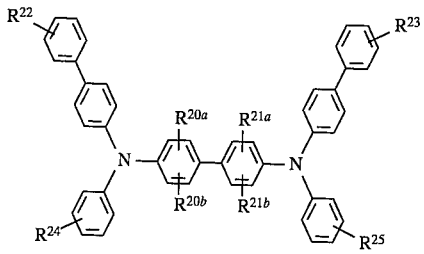

wherein $R^{20a}$, $R^{20b}$, $R^{21a}$, $R^{21b}$, $R^{22}$ and $R^{23}$ are the same or different and indicate a hydrogen atom or an alkyl group; and $R^{24}$ and $R^{25}$ are the same or different and indicate a hydrogen atom, an alkyl group or an aryl group which may have a substituent.

6. The electrophotosensitive material according to claim 5, wherein the organic photosensitive layer further contains an electron accepting compound having an oxidation-reduction potential of −0.8 to −1.4 V.

7. The electrophotosensitive material according to claim 5, wherein the electric charge generating material is a phthalocyanine pigment.

8. An electrophotosensitive material comprising a conductive substrate and an organic photosensitive layer provided on the conductive substrate, the organic photosensitive layer containing tryptoanthorine or a derivative thereof represented by the formula;

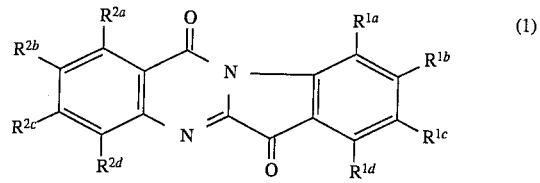

wherein $R^{1a}$, $R^{1b}$, $R^{1c}$, $R^{1d}$, $R^{2a}$, $R^{2b}$, $R^{2c}$, and $R^{2d}$ are the same or different and indicate a hydrogen atom, an alkyl group or a halogenated alkyl group; provided that $R^{1a}$, $R^{1b}$, $R^{1c}$, and $R^{1d}$ do not indicate a hydrogen atom, simultaneously.

* * * * *